US012607562B2

(12) United States Patent
Smith et al.

(10) Patent No.: US 12,607,562 B2
(45) Date of Patent: Apr. 21, 2026

(54) SYSTEM AND METHOD FOR MEASURING, STORING, COLLATING, AND DISPLAYING VIBRATIONAL SPECTRA OF LIVING CELLS AND TISSUE USING DIGITAL COMPARATIVE PRECISION NOISE REDUCTION

(71) Applicant: Digital Harmonic LLC, Columbia, MD (US)

(72) Inventors: Paul Reed Smith, Annapolis, MD (US); Mason Baron, Laurel, MD (US); William G. Nelson, Cockeysville, MD (US); Shane G.W. Morris, Baltimore, MD (US); Sandor Szalay, Baltimore, MD (US); Jonathan B. Coulter, Baltimore, MD (US); Frederick M. Slay, Okatie, SC (US); Scott Haiges, Lancaster, PA (US)

(73) Assignee: Digital Harmonic LLC, Columbia, MD (US)

( * ) Notice: Subject to any disclaimer, the term of this patent is extended or adjusted under 35 U.S.C. 154(b) by 142 days.

(21) Appl. No.: 18/661,228

(22) Filed: May 10, 2024

(65) Prior Publication Data

US 2025/0347623 A1 Nov. 13, 2025

(51) Int. Cl.
*G01N 21/64* (2006.01)
*G01N 33/483* (2006.01)
(Continued)

(52) U.S. Cl.
CPC ..... *G01N 21/6428* (2013.01); *G01N 33/4833* (2013.01); *G06T 5/70* (2024.01); *G06T 11/206* (2013.01); *G01N 2021/6439* (2013.01)

(58) Field of Classification Search
None
See application file for complete search history.

(56) References Cited

U.S. PATENT DOCUMENTS 3,761,187 A 9/1973 Dittrich et al.
4,453,181 A 6/1984 Munakata et al.
(Continued)

FOREIGN PATENT DOCUMENTS

CN 1279054 A 1/2001
CN 103584835 B 5/2015
(Continued)

OTHER PUBLICATIONS

Park et al., "Refractive index maps and membrane dynamics of human red blood cells parasitized by Plasmodium falciparum," Proceedings of the National Academy of Sciences of the U.S.A. (PNAS), vol. 105, No. 37, 13730, dated Sep. 16, 2008, 6 pages.
(Continued)

*Primary Examiner* — Hoon K Song
(74) *Attorney, Agent, or Firm* — Sterne, Kessler, Goldstein & Fox P.L.L.C.

(57) ABSTRACT

Disclosed are systems and methods for measuring vibrational spectra of living cells and conducting comparative precision noise reduction (CPNR). A system according to some embodiments can include at least one photon source configured to generate a first photon beam that passes through living objects in medium and a second photon beam that passes through a reference medium. Detectors can be configured to produce first and second analog signals representative of the vibrational spectra of the objects and the noise spectra of the reference medium. At least one analog-to-digital converter can be configured to convert the first and second analog signals into first and second digital representations. At least one processor can be configured to define one or more reference events from the second digital representation, identify one or more very similar matching events from the first digital representation, and remove matching events from the first digital representation data.

29 Claims, 17 Drawing Sheets

(51) Int. Cl.
  G06T 5/70 (2024.01)
  G06T 11/20 (2006.01)

(56) References Cited

U.S. PATENT DOCUMENTS

| | | | |
|---|---|---|---|
| 5,117,110 A | 5/1992 | Yasutake | |
| 6,073,722 A | 6/2000 | Babuke et al. | |
| 6,212,292 B1 | 4/2001 | Soares | |
| 6,405,359 B1 | 6/2002 | Tseng et al. | |
| 6,766,288 B1 | 7/2004 | Smith | |
| 7,286,229 B1 | 10/2007 | Meeks | |
| 8,480,584 B2 | 7/2013 | Kanayama et al. | |
| 8,620,976 B2 | 12/2013 | Smith et al. | |
| 9,279,839 B2 | 3/2016 | Smith et al. | |
| 9,390,066 B2 | 7/2016 | Smith et al. | |
| 9,412,179 B2 | 8/2016 | Oshima et al. | |
| 9,572,497 B2 | 2/2017 | Razansky et al. | |
| 9,600,445 B2 | 3/2017 | Smith et al. | |
| 9,610,018 B2 | 4/2017 | Gulati et al. | |
| 11,293,853 B2 | 4/2022 | Smith et al. | |
| 2004/0214243 A1 | 10/2004 | Burshteyn et al. | |
| 2005/0057756 A1 | 3/2005 | Fang-Yen et al. | |
| 2005/0105097 A1 | 5/2005 | Fang-Yen et al. | |
| 2005/0214167 A1 | 9/2005 | Archibald et al. | |
| 2009/0251706 A1 | 10/2009 | Rembe et al. | |
| 2011/0024630 A1 | 2/2011 | Sundaram et al. | |
| 2011/0306857 A1 | 12/2011 | Razansky et al. | |
| 2012/0196356 A1 | 8/2012 | Wagner et al. | |
| 2014/0253713 A1 | 9/2014 | Zhai et al. | |
| 2017/0258332 A1 | 9/2017 | Wynn et al. | |
| 2020/0033259 A1 | 1/2020 | Krausz et al. | |
| 2022/0228969 A1* | 7/2022 | Smith | G01N 15/1484 |
| 2024/0393246 A1* | 11/2024 | Petisce | G01N 31/221 |
| 2025/0189362 A1* | 6/2025 | Iwasaki | G06T 5/50 |

FOREIGN PATENT DOCUMENTS

| | | |
|---|---|---|
| CN | 106323447 A | 1/2017 |
| EP | 0980672 A1 | 2/2000 |
| EP | 3076860 A1 | 10/2016 |
| JP | 2004144639 A | 5/2004 |
| JP | 2009297206 A | 12/2009 |
| JP | 2013506145 A | 2/2013 |
| JP | 2017012197 A | 1/2017 |
| WO | 2012068287 A2 | 5/2012 |

OTHER PUBLICATIONS

Fitzgerald, M., "Vibrating Cells Disclose Their Ailments," MIT Technology Review, accessed at https://www.technologyreview.com/2008/09/09/33557/vibrating-cells-disclose-their-ailments/, published Sep. 9, 2008, 3 pages.

Fraldi et al., "A frequency-based hypothesis for mechanically targeting and selectively attacking cancer cells," J. R. Soc. Interface, 12(111):1-16 (Aug. 2015).

Holmes et al., "Synchronized mechanical oscillations at the cell-matrix interface in the formation of tensile tissue," Proceedings of the National Academy of Sciences of the U.S.A., 115(40):E9288-E9297 (Aug. 2018).

Jaganathan et al., "Natural frequency of cancer cells as a starting point in cancer treatment," Current Science, 110(9):1828-1832 (May 2016).

Medeiros et al., "An electrical method to measure low-frequency collective and synchronized cell activity using extracellular electrodes," Sensing and Bio-sensing Research, 10:1-8 (Jun. 2016).

Notbohm et al., "Cellular Contraction and Polarization Drive Collective Cellular Motion," Biophysical Journal, 110:2729-2738 (Jun. 2016).

Sanyour et al, "Spontaneous oscillation in cell adhesion and stiffness measured using atomic force microscopy," Nature Scientific Reports, 8:1-10 (Feb. 2018).

International Search Report and Written Opinion directed to related International Patent Application No. PCT/US2019/047880, mailed Dec. 2, 2019, 19 pages.

Jaross, W., "Are Molecular Vibration Patterns of Cell Structural Elements Used for Intracellular Signalling?," The Open Biochemistry Journal, vol. 10, No. 1, 2016, pp. 12-16.

Pienta, K.J., et al., "Cellular Harmonic Information Transfer Through a Tissue Tensegrity-Matrix System," Medical Hypotheses, vol. 34, No. 1, 1991, pp. 88-95.

Myrdal, S.E., et al., "An Agent or Agents Produced by Virus-transformed Cells Cause Unregulated Ruffling in Untransformed Cells," The Journal of Cell Biology, vol. 102, No. 4, 1986, pp. 1224-1229.

Partin, A., et al., "Fourier Analysis of Cell Motility: Correlation of Motility with Metastatic Potential," Proceedings of the National Academy of Sciences of the U.S.A., vol. 86, No. 4, 1989, pp. 1254-1258.

Vadalà, M. et al., "Mechanisms and Therapeutic Effectiveness of Pulsed Electromagnetic Field Therapy in Oncology," Cancer Medicine, vol. 5, No. 11, 2016, pp. 3128-3139.

Guo, F., et al., "Three-Dimensional Manipulation of Single Cells Using Surface Acoustic Waves," Proceedings of the National Academy of Sciences of the U.S.A., vol. 113, No. 6, 2016, pp. 1522-1527.

Nelson, S.L., et al., "Vibrational Profiling of Brain Tumors and Cells," Theranostics, vol. 7, No. 9, 2017, pp. 2417-2430.

Ding, X., et al., "Cell Separation Using Tilted-Angle Standing Surface Acoustic Waves," Proceedings of the National Academy of Sciences of the U.S.A., vol. 111, No. 36, 2014, pp. 12992-12997.

Rittner et al. "Visible light." Science Encyclopedia: Encyclopedia of Chemistry (2nd edition). Obtained at credoreference.com. (Year: 2016); 24 pages.

International Search Report and Written Opinion for International Patent Application No. PCT/US2025/027949, U.S. Patent and Trademark Office (USPTO), mailed Jul. 18, 2025, 11 pages.

* cited by examiner

Principal Spectral Signal POST Comparative Precision Noise Reduction Over 60 Seconds (PMM 3D)

Reference Spectral Signal Noise Over 60 Seconds (PMM 2D)

Principal Spectral Signal POST Comparative Precision Noise Reduction Over 60 Seconds (PMM 2D)

700C

730

708

Frequency 702

Time 704

706

800

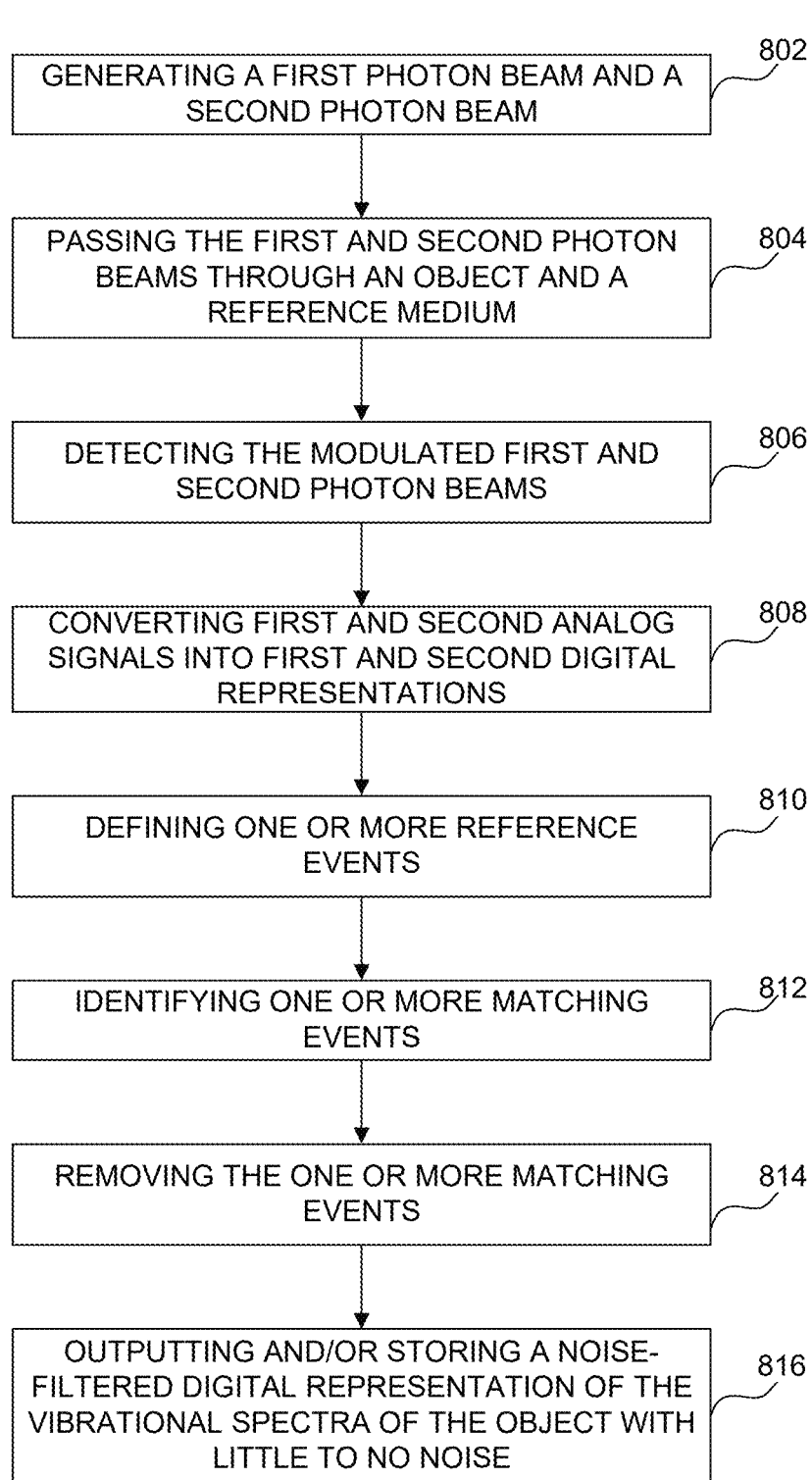

GENERATING A FIRST PHOTON BEAM AND A SECOND PHOTON BEAM — 802

PASSING THE FIRST AND SECOND PHOTON BEAMS THROUGH AN OBJECT AND A REFERENCE MEDIUM — 804

DETECTING THE MODULATED FIRST AND SECOND PHOTON BEAMS — 806

CONVERTING FIRST AND SECOND ANALOG SIGNALS INTO FIRST AND SECOND DIGITAL REPRESENTATIONS — 808

DEFINING ONE OR MORE REFERENCE EVENTS — 810

IDENTIFYING ONE OR MORE MATCHING EVENTS — 812

REMOVING THE ONE OR MORE MATCHING EVENTS — 814

OUTPUTTING AND/OR STORING A NOISE-FILTERED DIGITAL REPRESENTATION OF THE VIBRATIONAL SPECTRA OF THE OBJECT WITH LITTLE TO NO NOISE — 816

FIG. 8

SYSTEM AND METHOD FOR MEASURING, STORING, COLLATING, AND DISPLAYING VIBRATIONAL SPECTRA OF LIVING CELLS AND TISSUE USING DIGITAL COMPARATIVE PRECISION NOISE REDUCTION

FIELD

The present disclosure relates to noise reduction apparatuses, systems, and methods, for example, comparative precision noise reduction apparatuses, systems, and methods for measuring movements of live cells.

BACKGROUND

Cells and living tissue move and produce complex vibrational spectra/frequencies by their movements. Time-lapse video photography of this movement has severe limitations for real time measurements. In nature, such movements are generating vibrational signatures. Thus, it is desirable to measure this vibrational spectra of living tissue to provide new insights for the study and manipulation of cells and living tissue. It is also desirable to measure the cells' and living tissues' vibrational response to stimuli. However, current technology does not capture the vibrational signals and/or harmonics generated by the cells themselves. What is desired are systems and methods that capture signals without noise to isolate vibrational spectra of the cells and/or sub-components of the cells.

SUMMARY

Accordingly, there is a need to develop a system that greatly reduces or eliminates noise utilizing comparative precision noise reduction techniques to measure ultra-low amplitude vibrational spectra, signals, and waveforms of objects including living cells, tissue, blood, bacteria, viruses, fungi, or protozoa, whether normal or abnormal.

In some embodiments, a system for measuring vibrational spectra of objects comprises at least one photon source configured to generate a first photon beam and a second photon beam. A support device can be configured to support the objects in medium and a reference medium such that, in operation, the first photon beam passes through the objects, thereby directly modulating the first photon beam, and the second photon beam passes through the reference medium modulating the second photon beam. The system can include at least one detector configured to detect the modulated first and second photon beams and produce first and second analog signals representative of the resultant vibrational spectra of the objects in the medium and the resultant noise spectra of the reference medium. The system can include at least one analog-to-digital converter configured to convert the first and second analog signals into first and second digital representations. The processor can be configured to define one or more reference events from the second digital representation, each of the one or more reference events comprising a time characteristic, a frequency characteristic, and/or an amplitude characteristic. The processor can be further configured to identify one or more matching events from the first digital representation, each of the one or more matching events corresponding to a reference event of the one or more reference events. The processor can also be configured to remove the one or more matching events from the first digital representation, thereby outputting a noise-filtered digital representation of the vibrational spectra of the objects.

In some embodiments, the systems and methods disclosed herein are configured to discover, measure, and characterize the vibrational spectra produced by living tissue. The systems and methods disclosed herein are configured to measure the vibrational spectra produced by cells. The cells produce a complex array of frequencies and amplitude changes over time and show cell vibrational spectra movement in response to physiologically relevant stimuli (e.g., sex-steroid hormones, lipophilic factors, and glucose), drugs (e.g., tumor necrosis factor (TNF), taxanes, nocodazole, formaldehyde, etc.), electric stimulus, acids and bases, etc.

In some embodiments, the disclosed system measures the vibrational signals generated from the direct application of light through the object(s) itself. This allows for determination of direct vibrational signals generated not only by the object(s) as a single entity, but by subcellular structures (e.g., cell membranes, cell walls, cytoplasm, cytosol, actin filaments, microtubules, mitochondria, ribosomes, lysosomes, individual proteins, nuclei, etc.). This can be done using fluorescent labeling of the structures with chemical dyes or overexpression of fluorescent-labeled molecules of selected excitation and emission properties, and detecting these specific emission signals by restricting the signals measured at the level of the detected wavelengths.

This includes measuring infrasonic, sub-sonic, and sonic frequency ranges of movements, vibrations, cellular motion, harmonics, and/or frequencies of cells over a fixed and/or continuous time periods to capture the cells' dynamic vibrational spectra change over time. Analyzation of which sub-cellular entity produces which vibrational spectra is thus made possible as disclosed herein.

It should be recognized that the cellular movement whilst measurable requires extremely low-noise circuitry detector components, low-noise collimated light source(s), and high quality analog-to-digital conversion techniques to accurately capture the remaining light modulated signals. What is further disclosed is a method to measure various noise components common to both a principal and reference signal paths. These common noise components can be removed, e.g., algorithmically, in the digital domain from the principal signal path thereby improving the signal-to-noise ratio of the desired principal signal data. Additional noise reduction techniques may also be introduced to allow for the implementation of comparative precision noise reduction algorithms and the like.

Comparative precision noise reduction as disclosed herein is based on the reality that data from the principal signal path (which can include cells) represents mostly cell vibrational spectra with a percentage of noise, and that data derived from the reference signal path represents entirely noise as no cells are in this method in the reference signal path. A digital algorithmic function is performed on the reference signal path data that defines mathematically the noise types and parameters of the reference signal data, including times, amplitudes, frequencies, harmonics and other domain information of the noise. These defined noise parameters are then compared to the principal signal path data. Any identified similar data (e.g., within predetermined threshold(s)) in the principal signal path data relative to the reference signal path data in time, amplitude, frequency, and harmonics is then removed algorithmically (e.g., subtracted) from the principal signal path data, thereby producing cell vibration data that is almost completely devoid of noise produced from external movement, electronics, light, electromagnetic fields, or any other source of noise. Thresholds shall include and not limited to delta time and/or delta frequency and/or delta amplitude and/or delta harmonic content and/or delta domain data.

Additionally, the same or substantially similar systems to those used for comparative precision noise reduction can be configured to compare data from two different signal paths (e.g., as gathered using primary and reference photon beams), for example, that each include respective cells. The comparison of such data can be used to identify differences between cells, for example, differences between normal cells and abnormal cells (e.g., diseased, such as comparing healthy brain cells to unhealthy brain cells). Accordingly, the comparison of such data can be used to identify distinctive signal characteristics for a particular category of cells (e.g., glioblastoma (GBM) brain cells). Further features and advantages of the systems and methods disclosed herein, as well as the structure and operation of various implementations of the systems and methods, are described in detail below with reference to the accompanying drawings. It is noted that this disclosure is not limited to the specific implementations described herein. Such implementations are presented herein for illustrative purposes only. Additional modifications may be apparent to persons skilled in the relevant art(s) based on the teachings contained herein.

BRIEF DESCRIPTION OF THE DRAWINGS

The accompanying drawings/figures, which are incorporated herein and form part of the specification, illustrate the present disclosure and, together with the description, further serve to explain the principles of the present disclosure and to enable a person skilled in the relevant art(s) to make and use the present disclosure.

FIG. 8 is a flow diagram illustrating a method for measuring vibrational spectra of an object, according to some embodiments.

Figure 1:
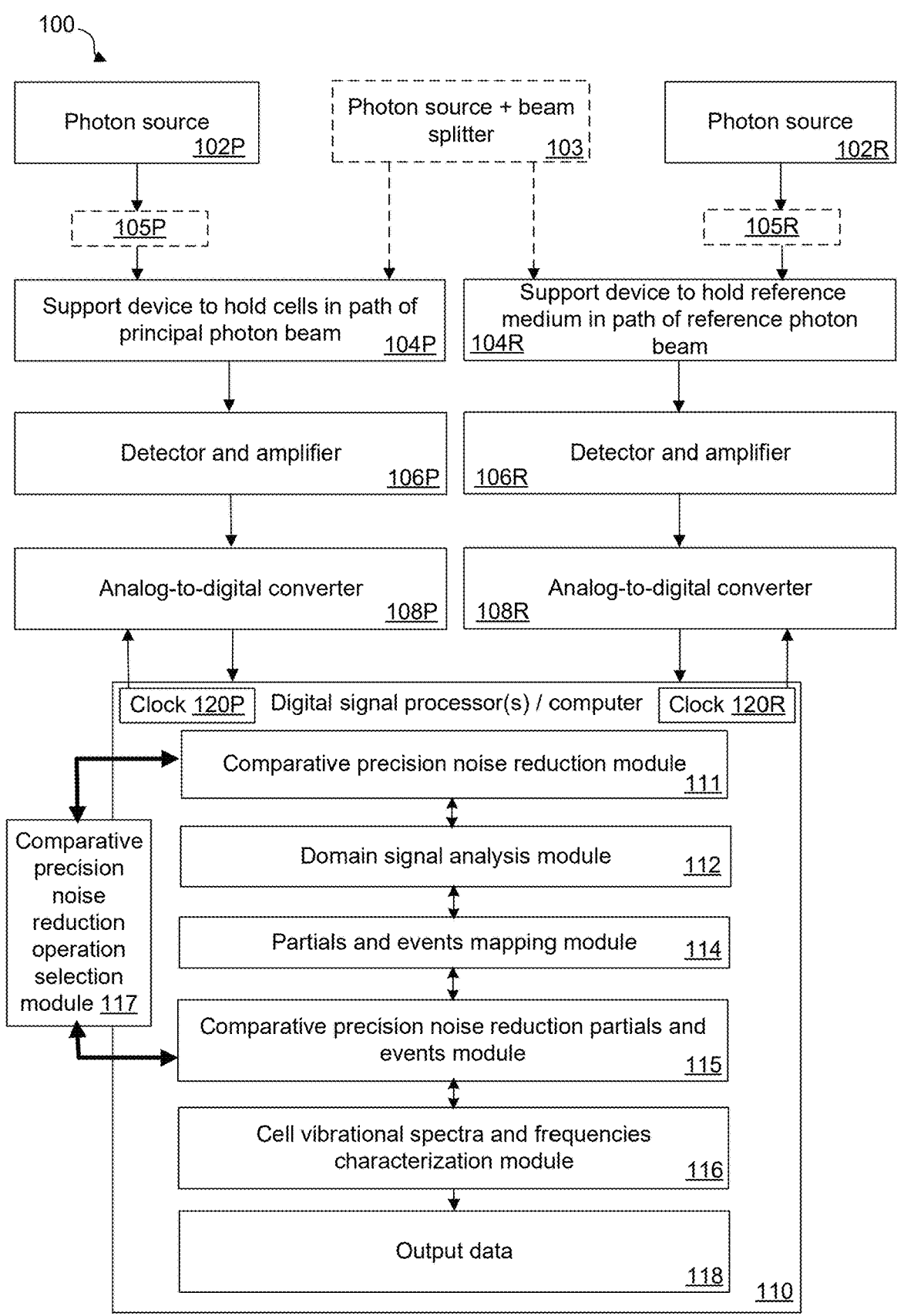
FIG. 1 is a block diagram illustrating a system for measuring vibrational spectra of an object, according to some embodiments.

The features and advantages of the present disclosure will become more apparent from the detailed description set forth below when taken in conjunction with the drawings. Unless otherwise indicated, the drawings provided throughout the disclosure should not be interpreted as to-scale drawings. Additionally, the text included in the illustrated block diagrams is provided as an example and is not intended to specifically limit any given step or element of the invention(s) described herein.

DETAILED DESCRIPTION

Although specific configurations and arrangements may be discussed, it should be understood that this is done for illustrative purposes only. A person skilled in the pertinent art will recognize that other configurations and arrangements can be used without departing from the spirit and scope of the present disclosure. It will be apparent to a person skilled in the pertinent art that this disclosure can also be employed in a variety of other applications beyond those specifically mentioned herein. It should be appreciated that the particular implementations shown and described herein are examples and are not intended to otherwise limit the scope of the disclosure in any way.

All numbers in this description indicating amounts, ratios of materials, physical properties of materials, and/or use are to be understood as modified by the word "about," except as otherwise explicitly indicated.

The term "about" as used herein indicates the value of a given quantity varies by up to about +50% of the value. For example, "about 100 nm" encompasses a range of sizes from about 75 nm to about 125 nm, inclusive.

The following definitions are used herein. The disclosure and definitions listed in U.S. Pat. No. 11,293,853 B2, issued Apr. 5, 2022, is hereby incorporated by reference herein in its entirety.

Comparative Precision Noise Reduction (CPNR): One or more algorithmic methods to selectively remove noise components from signals based on synchronous data collection. CPNR is a signal processing technique that is highly effective in suppressing or eliminating additive interference or noise spectra corruption of a target signal received at the principal detector in certain common situations. CPNR is searching events for common time areas and/or common frequency areas and/or common amplitude amounts and/or common harmonic frequency and rankings. Measured second beam noise events in a data stream may be of interest for removing from the first beam data because the event's profile(s) similarity match a known noise time, frequency, and/or amplitude profiles stored in memory. Matching and/or collating profiles may be approximate or may simply involve matching a profile's time, frequency, and/or amplitude characteristic. These similar events are herein defined as "matching." Comparing the data in both data streams for matches can utilize artificial intelligence, machine learning, and/or the PMM, or other noise comparison techniques.

Delta: A range as applied to any value movement.

Consistent Light Source: A producer of a low-noise light beam.

Collimated Light: Light that has been collimated. This can be accomplished with optics, lasers, physical restrictors, and the like, as would become apparent to persons skilled in the art.

Low-Amplitude Noise: As used herein, "low-noise" refers to components that are selected to reduce the amount of noise (e.g., thermal noise) inherently generated by a cell measuring system. In some embodiments, as used herein, "low-noise" refers to a noise level (e.g., thermal noise) at or below the shot noise of the component (e.g., optical source, detector, analog-to-digital converter, etc.). For example, semiconductor noise can be specified as 2.9-nV/√Hz voltage noise density and 6-fA/√Hz current noise density, for example, based on a measurement of noise from an operational amplifier, and is defined as ultra-low noise.

Domain Identification: As disclosed in U.S. Pat. No. 9,279,839, the disclosure of which is incorporated by reference herein in its entirety.

Modulate: As used herein with respect to how measurements of cells are captured, the cells are exposed to and thus modulate the incident (optionally collimated) photon beam and vary how much of the beam is blocked, absorbed, or deflected. This modulation is measured as changing amplitude of the beams over time.

Objects: Living cells, tissue, blood, bacteria, viruses, fungi, or protozoa, whether normal or diseased.

Precision Measuring Matrix (PMM): As disclosed in U.S. Pat. No. 8,620,976, the disclosure of which is incorporated by reference herein in its entirety.

Wetted special slip (WSS): A top configured to be disposed on a medium and function like a custom designed slip to fit an accompanying object petri dish, or the like container. The WSS allows the surface of the medium contained in the petri dish to wet the underside of the WSS, which is similar in function to a microscope slip. The WSS or plural WSSs are disposed directly on the medium and are configured to eliminate any surface tension noise such that incident beams are not inadvertently modulated by surface tension. A WSS may appear as a type of lid for a petri dish. The WSS becomes wet when it is placed on the petri dish to the depth of the medium that is in the dish so the bottom of the WSS is slightly in the medium (with no bubbles).

Any conflict between any reference cited herein and the specific teachings of this specification shall be resolved in favor of the latter. Likewise, any conflict between an art understood definition of a word or phrase and a definition of the word or phrase as specifically taught in this specification shall be resolved in favor of the latter.

Technical and scientific terms used herein have the meaning commonly understood by one of skill in the art to which the present application pertains, unless otherwise defined. Reference is made herein to various methodologies and materials known to those of skill in the art.

Overview

Disclosed is a system and method to measure and characterize the vibrational spectra produced by living objects. The vibrational spectra produced by such objects are of extraordinarily low amplitude. The subject of this disclosure is systems and methods that are extremely sensitive and are configured to detect and measure frequencies at or below the noise level produced by the implemented photon source(s), the detector(s), and the surrounding environment. Synchronous data is acquired by sensing movement of two or more signal paths.

The systems and methods for measuring these spectra, for example, the computer software features of this disclosure, can employ signal processing techniques disclosed in one or more of the following U.S. Patents, the contents of which are incorporated herein by reference in their entireties: U.S. Pat. No. 6,766,288 B1, issued Jul. 20, 2004 and titled "Fast Find Fundamental Method"; U.S. Pat. No. 8,620,976 B2, issued Dec. 31, 2013 and titled "Precision Measurement of Waveforms"; U.S. Pat. No. 9,600,445 B2, issued Mar. 21, 2017 and titled "Precision Measurement of Waveforms"; U.S. Pat. No. 9,390,066 B2, issued Jul. 12, 2016 and titled "Precision Measurement of Waveforms Using Deconvolution and Windowing"; and U.S. Pat. No. 9,279,839 B2, issued Mar. 8, 2016 and titled "Domain Identification and Separation for Precision Measurement of Waveforms."

In some embodiments, components of the system are mounted on a sound absorber effective to very low frequencies. In some embodiments, the system uses at least one low-noise photon source with controlled photon beam level amplitude and collimated photon beam diameter, to shine a beam of photons by and through living cells. The beam strength can either be constant, interrupted, or otherwise modulated to facilitate the analysis. This enables various other analysis modes, such as employing a phase-locked loop configuration or operating in a frequency mixer mode, shifting the detected oscillations of the cell to a different frequency band by chopping the frequency of the light. Light sources to produce the beams, can be lasers, incandescent bulbs, LEDs, plasma sources, and the like, as would become apparent to persons skilled in the art.

As the cells move, they are exposed to and thus modulate the incident collimated photon beam and vary how much of the beam is blocked, absorbed, or deflected. This modulated photon beam is then detected, quantified, and analyzed, revealing details about how the cells move, vibrate, and/or undulate. The beam can be two separately generated beams or a single beam optically split into two beam branches, one for measuring the cell/tissue that is directed toward a single or multiple pixel detector producing a principal signal P(t), and the other as a reference for noise reduction, with the reference beam being directed toward a single or multiple pixel detector (either the same or a different detector) producing a reference signal R(t). After being modulated by the cell/tissue, the principal photon beam may be split again into several beams, for example, one for an eye piece, one for a low light camera (for alignment purposes), and one for the single or multiple pixel detector. Each single or multiple pixel detector(s) produces a signal voltage output as noted—V(t)—as a function of time. Ultralow noise detectors such as photon detectors can be, but are not limited to PIN photodiodes, avalanche photodiodes (APD), Schottky barrier photodiodes, photoconductor photon multipliers, superconducting nanowire single photon detectors (SNSPD), quantum well and quantum dot photodetectors, charge coupled devices (CCD), CMOS detectors, or the like, as would become apparent to persons of skill in the art. The detector or detectors can be located apart from the support device (discussed below) using fiber optics, light pipes, or the like.

In some embodiments, the system can be used to measure not only the overall or integrated movement of cells and tissues, but also sub-cellular structures and conditions that may have characteristic and meaningful movement. For example, a fluorescent marker (e.g., molecules, also referred to as tags, and which may comprise dyes) can be exploited to emit light at longer wavelengths than the excitation wavelength (e.g., about 500 nm). Light emitted from the sub-cellular structure(s) is passed through long pass dichroic mirrors (specifically directing light of wavelengths greater than a set value) to pass on to bandpass filters. These filters allow only emitted light of specified wavelength to reach the detector, providing detection of light specifically from the sub-cellular structure(s). The resulting signal will provide the vibrational spectra of sub-cellular structures of interest while blocking the excitation light.

Each analog output from the two paths is then fed into analog-to-digital converters that can be synchronous in operation. The digital synchronous data can be stored in computer memory or disk drive or data storage device (e.g., non-volatile storage) for later use. The digital synchronous data is algorithmically compared and in some embodiments, comparative precision noise reduction (CPNR) can be implemented. In some embodiments, CPNR can be implemented by use of a precision measuring matrix (PMM) to identify like properties in the P(t) and R(t) signals. The result is a single stream of data that is representative of a cellular signal S(t) fed into a computer or data storage device (e.g., non-volatile storage). The PMM can be used to identify partials and events, and subsequently can be used to produce associated histograms that yield results as aggregations of frequency events over time, and potential harmonics. In some embodiments, Domain Identification of signals can be performed. This can be done in real-time or by accessing the recorded data. The system and method thus provides a digitized representation of the vibrational spectra of the cells/living tissue. The method(s) of analysis are not limited to a single type of discovery. Multiple signal paths may be used to support CPNR techniques. Note that the longer the detection period is in time (recording the signal) the better the signal to noise ratio can be. Signals can be adjusted (e.g., stopped) through chemical fixation of the cells/tissue, for example, by a compound like formaldehyde (which can reduce and/or halt cellular vibrational spectra/movement).

The design of the system described herein was driven by a number of factors. Such factors can include that the cells are live, and must be studied live, so even extended observations should not harm the cells. This places constraints on the intensity of the incident light/photon beam, significantly decreasing the signal-to-noise of the measurements. Likewise, the correct temperature of the test in vitro system must be maintained for the cells/tissue to remain viable during the testing. Also, the vibrations of the cells can be measured up to frequencies in the few hundred Hz range. Thus, we must be able to read the detectors at such rates. The signal-to-noise ratio of the measured signal should be close to the theoretical maximum, i.e., the shot noise due to the number of discrete single or multiple pixel photo-electrons detected from the incident light beam. Additional sources of noise must also be reduced or eliminated. And the surface of the growth medium influences the noise of the system. Since the current disclosure relies on the accurate measurement of the remaining photon beam to obtain S(t), the surface diffraction is mitigated using a custom petri dish lid that is wetted to contact the top of the medium.

These constraints essentially limit the practical use of many-pixel imaging devices, like high-speed video cameras or many-pixel standard CCDs. However, the current state of the art in QCMOS multiple pixel cameras may be utilized. In some embodiments, the systems and methods presented herein can use a single pixel detector. In some embodiments, the system and methods presented herein can use a multiple pixel detector.

DESCRIPTION OF EXEMPLARY SYSTEMS AND METHODS

FIG. 1 illustrates an example system 100 for measuring vibrational spectra of cells or living tissue, according to some embodiments. In the following description the suffix "P" designates the principal signal path and the suffix "R" designates the reference signal path. In some embodiments, system 100 can include separate photon sources 102P and 102R configured to generate a principal photon beam and a reference photon beam. In some embodiments, system 100 can include a single photon source and beam splitter 103 configured to generate the principal photon beam and the reference photon beam. In some embodiments, photon sources 102P, 102R, and/or 103 can be low-noise collimated photon beam sources. In some embodiments, photon sources 102P and 102R can be statically coupled (e.g., physically fixed or bolted together using any mechanical means as would become apparent to persons skilled in the art). In some embodiments, photon sources 102P, 102R, and/or 103 can include a light-emitting diode (LED), a laser, or a combination thereof.

In some embodiments, system 100 can include a support device 104P configured to support the cells and/or living tissue and a support device 104R configured to support a reference medium. In some embodiments, support device 104P and 104R can be a single support device such that the single support device is common to both the principal and reference signal paths. In operation, the principal photon beam 102P can pass through the cells/living tissue disposed in medium, thereby directly modulating the principal photon beam, and the reference photon beam can pass through the reference medium, thereby directly modulating the reference photon beam (i.e., the reference photon beam is modulated with signal noise from the environment). In some embodiments, the reference medium can be the same medium that surrounds the cells and/or living tissue objects (e.g., air, a growth medium, and/or walls of a petri dish). But the reference medium omits the cells and/or living tissue objects. In some embodiments, the reference medium is identical or nearly identical to the medium the principal photon beam passes through, apart from the absence of cells/living tissue. In some embodiments, however, other cells/living tissue can be placed in the reference signal path such that the vibrational spectra of different cells/living tissue may be compared.

In some embodiments, a WSS can be disposed on the medium suspending the objects and/or on the reference medium, as illustrated at 105P and 105R. The WSS or plural WSSs are configured to eliminate any surface tension noise such that incident beams are not inadvertently modulated by surface tension.

In some embodiments, system 100 can include a detector and ultralow noise amplifier 106P configured to detect and amplify the modulated principal photon beam that has passed through the cells/living tissue. Likewise, in some embodiments, system 100 can include a detector and amplifier 106R configured to detect and amplify the modulated reference photon beam that has passed through the reference medium. In some embodiments, detectors and amplifiers 106P, 106R can be a single detector and/or amplifier such that the single detector and/or amplifier is common to both the principal and reference signal paths. In some embodiments, the detectors (or single detector) can be configured to produce a principal analog signal representative of the vibrational spectra of the cells/living tissue and a reference analog signal representative of the resultant noise spectra of the reference medium. It should be understood that "representative of the vibrational spectra of the cells/living tissue" need not refer to a signal that purely represents vibrational spectra of cells/living tissue; rather, the signal may include noise as well.

In some embodiments, the detectors (or single detector) can include single or multiple pixel detectors. In some embodiments, the detectors (or single detector) can be configured to operate over a broad frequency range (e.g., about 0.1 Hz to about 300 Hz).

The streamed signals from the detectors and amplifiers 106P, 106R can pass into a ultralow noise A/D converters 108P and 108R, as would become apparent to persons skilled in the art. In some embodiments, A/D converters 108P and 108R can be a single A/D converter, for example, a multichannel A/D converter. A/D converters 108P and 108R can be configured to convert the principal analog signal and the reference analog signal into principal and reference digital representations, respectively. In some embodiments, the principal digital representation and/or reference digital representation (e.g., real-time digital representation) is not manipulated or changed in any way (e.g., is processed such that there is no change from the analog frequency and/or amplitude data).

The principal and reference digital representations can then be passed on to processor(s) 110. Processor(s) 110 can be digital signal processor(s) and can be part of a computer. In some embodiments, processor(s) 110 can utilize one or more synchronized clocks to synchronize the synchronous data from the two A/D converters 108P and 108R. In some embodiments, the synchronized clock can include a principal clock 120P used to measure a time period data is received at and/or processed by A/D converter 108P. Likewise, in some embodiments, the synchronous clock can include a reference clock 120R used to measure a time period data is received at and/or processed by A/D converter 108R. In some embodiments, these two clocks can be synchronized (i.e., timers start at the same instant) such that data from the principal signal path and data from the reference signal path are timestamped identically or nearly identically (e.g., the timestamp reflects an absolute time the data was received at and/or processed by a given A/D converter 108P, 108R). It should be understood that some tolerances exist, but the synchronization of clocks 120P and 120R can increase the accuracy of comparisons of data from the principal and reference signal paths, for example, by ensuring processing time differences between A/D converter 108P and A/D converter 108R do not skew timestamps of the signal data.

The received data can be stored for later analysis. One of the functions of the processor(s) 110 is to apply CPNR techniques to remove any common noise artifacts that exist in both the signals P(t) and R(t) from the signal P(t). In some embodiments, a CPNR operation selection module 117 allows for the selection of the operation of one or more CPNR algorithms to be implemented. The concept of CPNR can implement any algorithmic function, and the discussion of example algorithms provided herein should not be interpreted to limit CPNR to any particular algorithm.

In some embodiments, processor(s) 110 can be configured to perform operations comprising: 1) defining one or more reference events from the reference digital representation, each of the one or more reference events including a time characteristic, a frequency characteristic, and an amplitude characteristic; 2) identifying one or more matching events from the principal digital representation, each of the one or more matching events corresponding to a reference event of the one or more reference events; and 3) removing the one or more matching events from the principal digital representation, thereby outputting a noise-filtered digital representation of the vibrational spectra of the cells/living tissue with little to no noise.

The term "event" should not be interpreted to mean that a PMM is used in all cases to characterize the principal and reference digital representations. Instead, the term "event" should be understood to mean any pattern of data (for example, a continuous line as shown in the graph of FIG. 5B) quantifiable in time, frequency, and/or amplitude that can be identified from the principal or reference digital representations. Further, it should be understood that the term "digital representation" can refer to anything from the raw output of the A/D converter(s) 108P, 108R to manipulated or otherwise processed or filtered digital output data.

To support the above operations, processor(s) 110 can run various software modules for analyzing data. A signal analysis module 112 can be used to characterize time, frequency, and amplitude of a signal including the presence of harmonically related frequencies. Partials and events mapping module 114 can be used to map the received signals to partials and events. CPNR partials and events module 115 can implement a PMM in noise reduction (e.g., use a PMM to define partials and events that are later compared). Cell vibrational spectra and frequencies characterization module 116 can be used to characterize the vibrational spectra and frequencies emitted by the cells/tissue over a given period of time. Ultimately, system 100 can provide output data 118 that can be stored in a memory and/or provided to a display. The output data 118 can include the vibrational spectra of the cells/tissue for a given time period, or an analysis of the vibrational spectra as it changes over time. The data can be stored in digital file format, transmitted electronically, or hard copy outputted. In some embodiments, output data 118 can be a noise-filtered digital representation of the vibrational spectra of the cells/living tissue with little to no noise.

In some embodiments, system 100 can identify and remove one or more events based on a predetermined threshold. For example, processor(s) 110 can define one or more reference events from the reference digital representation in time, frequency, and amplitude (e.g., $t_i$, $f_i$, $a_i$), identify one or more matching events from the principal digital representation within one or more predetermined time, frequency, and amplitude thresholds and/or deltas (e.g., $\Delta t$, $\Delta f$, $\Delta A$), and digitally remove the one or more matching events from the principal digital representation. In some embodiments, the one or more predetermined thresholds can be one or more ranges of time, frequency, and amplitude (e.g., $\Delta t$, $\Delta f$, $\Delta A$). In some embodiments, the one or more predetermined thresholds can be one or more percentages of time, frequency, and amplitude relative to a corresponding reference event (e.g., $\Delta t = \pm 1\%$ of $t_i$, $\Delta f = \pm 5\%$ of $f_i$, $\Delta A = \pm 5\%$ of $A_i$). In some embodiments, processor(s) 110 can identify one or more matching events based on whether a corresponding reference event is within a predetermined frequency span (e.g., $\Delta f$) over a specified time period. Alternatively or additionally, in some embodiments, processor(s) 110 can identify one or more matching events based on whether a corresponding reference event is within a predetermined amplitude span (e.g., $\Delta A$) over a specified time period. In some embodiments, processor(s) 110 can identify one or more matching events based on whether a corresponding reference event is within a predetermined time span (e.g., $\Delta t$) over a specified time period. In some embodiments, processor(s) 110 can identify one or more matching events based on whether a corresponding reference event is within a predetermined frequency span (e.g., $\Delta f$) over a specified time period.

Figure 2:
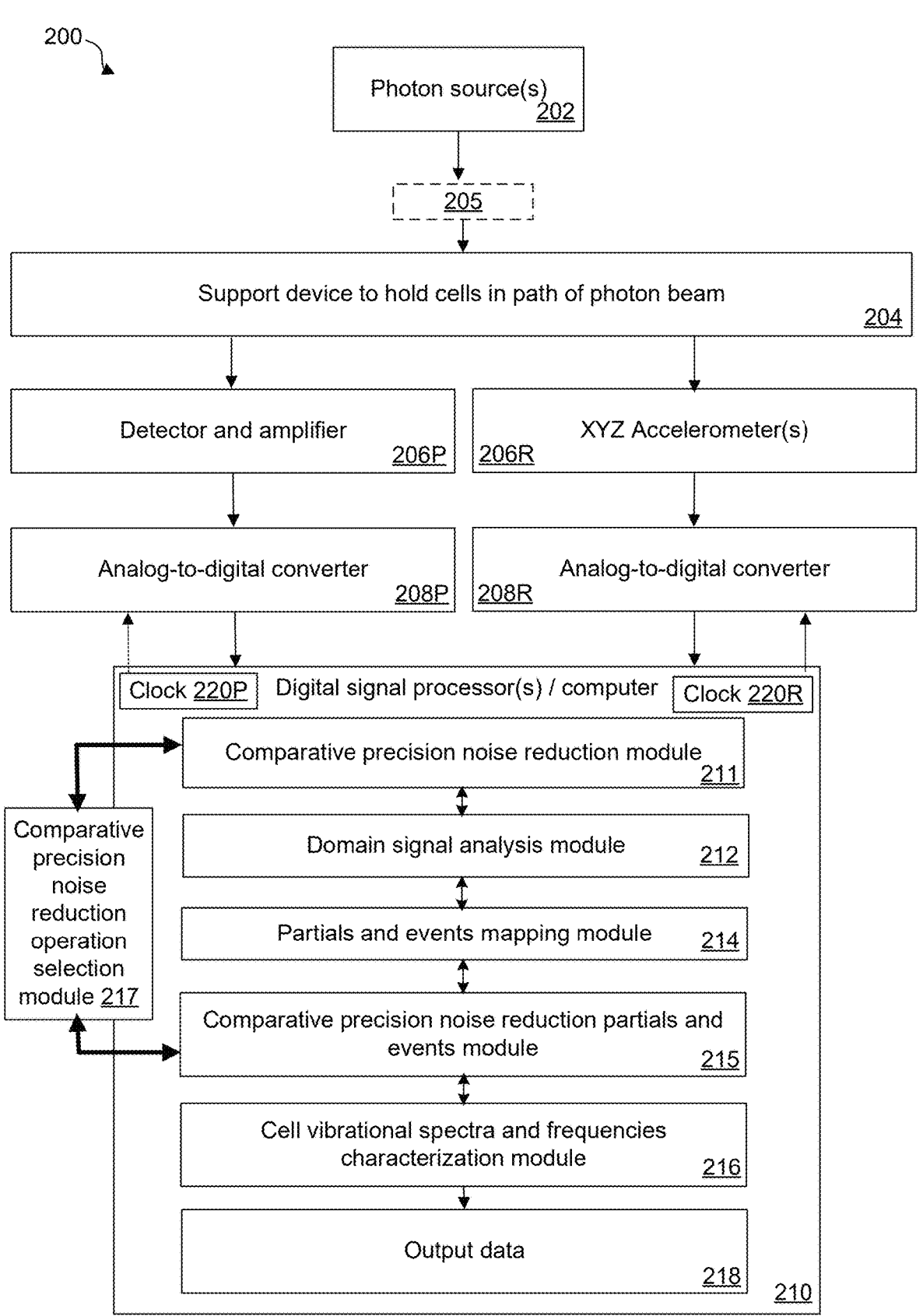
FIG. 2 is a block diagram illustrating a system for measuring vibrational spectra of an object, according to some embodiments.

FIG. 2 illustrates a second example system 200 for measuring vibrational spectra of cells or living tissue, according to some embodiments. In the following description the suffix "P" designates the principal signal path and the suffix "R" designates the reference signal path. In some embodiments, system 200 can include a photon source 202 configured to generate a photon beam. In some embodiments, photon source 202 can be a low-noise collimated photon beam source as discussed above. In some embodiments, photon source 202 can include an LED, a laser, or a combination thereof.

The embodiments of system 100 shown in FIG. 1, for example, and the embodiments of system 200 shown in FIG. 2 may be similar. Similar reference numbers are used to indicate features of the embodiments of system 100 shown in FIG. 1 and the similar features of the embodiments of system 200 shown in FIG. 2.

In some embodiments, system 200 can include a support device 204 configured to support the cells and/or living tissue. In some embodiments, support device 204 can be common to the principal signal path and the reference signal path. In operation, the photon beam can pass through the cells/living tissue, thereby directly modulating the photon beam.

In some embodiments, support device 204 is equipped with one or more sensors coupled to support device 204 and configured to detect one or more vibrations of support device 204. In some embodiments, a WSS can be used as illustrated at 205. In some embodiments, the one or more sensors can include one or more XYZ accelerometer(s) 206R, for example, one or more one ultra-sensitive, low-noise XYZ accelerometers. By "XYZ accelerometer(s)," it should be understood that the accelerometer(s) can measure acceleration along three-axes.

In some embodiments, system 200 can include a detector and amplifier 206P configured to detect and amplify the modulated photon beam that has passed through the cells/living tissue. In some embodiments, the detector can be configured to produce an analog signal representative of the vibrational spectra of the cells/living tissue. The detector can include a single or multiple pixel detector. In some embodiments, the detector can include a light pipe and/or light pipe detector. In some embodiments, the detector can be configured to operate over a broad frequency range (e.g., 0.1 Hz to 300 Hz). In some embodiments, the XYZ accelerometer(s) 206R can be connected to amplifier(s) and connected to A/D converter(s), for example, A/D converter 208R.

The streamed signals from the detector and amplifier 206P and XYZ accelerometer(s) 206R can pass into A/D converters 208P and 208R. In some embodiments, A/D converters 208P and 208R can be a single A/D converter, for example, a multichannel A/D converter. A/D converters 208P and 208R can be configured to convert the analog signal(s) principal and acceleration data (which can be analog acceleration data) into digital representations, respectively. In some embodiments, XYZ accelerometer(s) 206R can be digital accelerometer(s), such that they produce a digital representation of acceleration data, conversion from analog is unnecessary, and/or only one A/D converter 208P is required. In some embodiments, the principal digital representation and/or reference digital representation (e.g., real-time digital representation) is not manipulated or changed in any way (e.g., is processed such that there is no change from the analog frequency and/or amplitude data).

Similar processes as described above with reference to processor(s) 110 of system 100 shown in FIG. 1 can be conducted with processor(s) 210 of system 200 shown in FIG. 2 to determine output data 218 based on signals from detector and amplifier 206P and XYZ accelerometer(s) 206R.

In some embodiments, the systems and methods described herein can combine elements and techniques of system 100 and system 200. For example, in some embodiments, XYZ accelerometer(s) 206R (or other sensors) can be included in system 100 along with detectors and amplifiers 106 and can be coupled to support device(s) 104. This can increase the ability of system 100 to detect noise from the environment (e.g., movements of support device(s) 104) and remove such noise from any output data 118.

Figure 3:
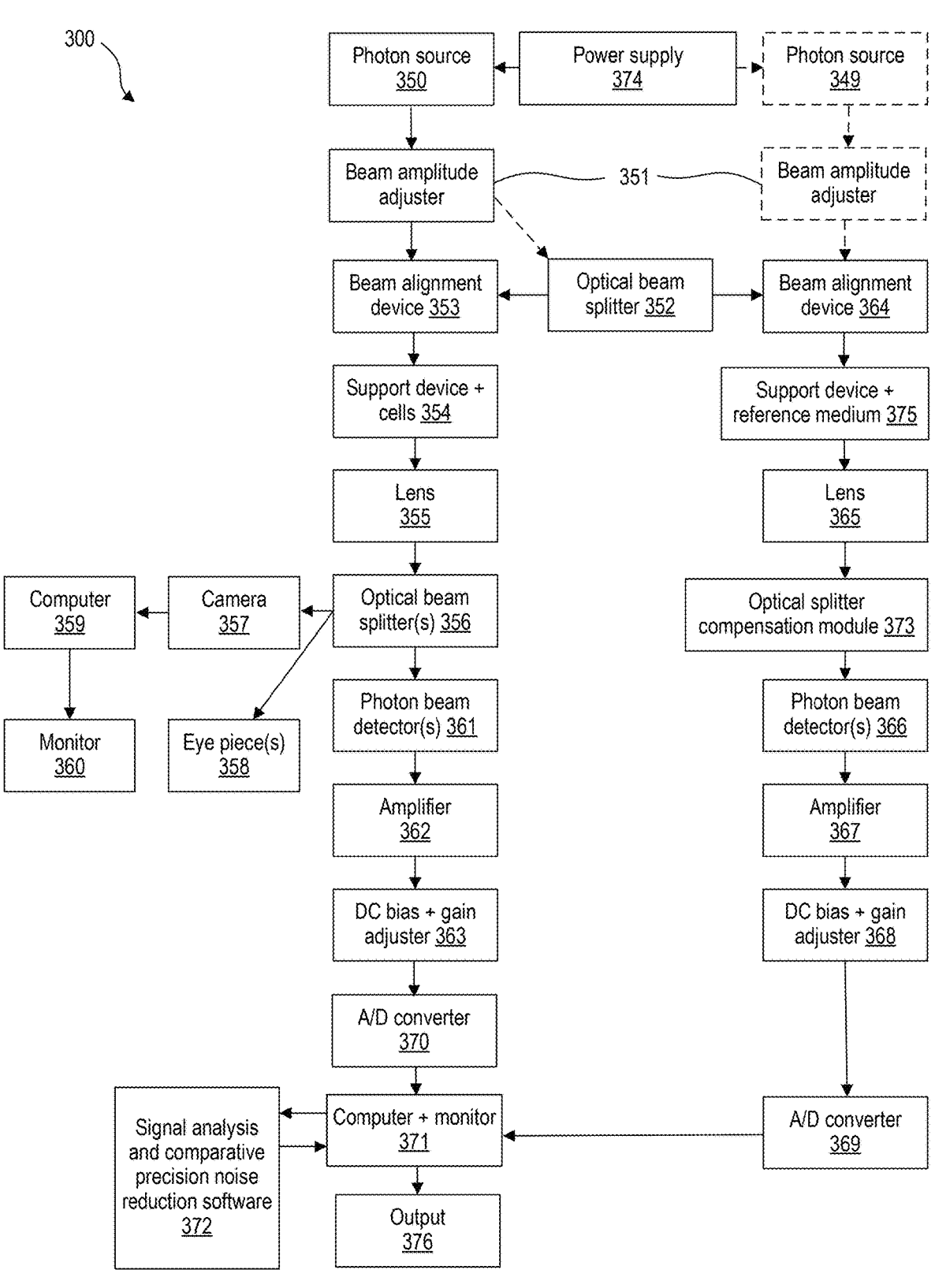
FIG. 3 is a block diagram illustrating a system for measuring vibrational spectra of an object, according to some embodiments.

FIG. 3 illustrates another system 300 for measuring vibrational spectra of cells or living tissue, according to some embodiments. While shown as a separate system, all or some of the components of system 300 can be integrated in system 100 and/or system 200.

The embodiments of system 100 shown in FIG. 1 and system 200 shown in FIG. 2, for example, and the embodiments of system 300 shown in FIG. 3 may be similar. Similar component names are used to indicate features of the embodiments of system 100 shown in FIG. 1 and system 200 shown in FIG. 2 and the similar features of the embodiments of system 300 shown in FIG. 3.

Similar to system 100, system 300 can include two photon sources 349 and 350 or a single photon source 350 and an optical beam splitter 352. The second of these options is illustrated in dotted lines in FIG. 3. In some embodiments, photon source 349 and/or photon source 350 can be the same as or similar to photon sources 102P, 102R, and/or 202 described with respect to FIGS. 1 and 2.

In some embodiments, system 300 can include a power supply 374 configured to power photon source 349 and/or photon source 350 to generate at least one collimated photon beam. In some embodiments, power supply 374 can be a low-noise power supply. In some embodiments, power supply 374 can be a DC battery or a low-noise DC power supply. While FIG. 3 shows power supply 374 powering photon source 349 and/or photon source 350, the same or a different power supply can power one or more of photon beam detector(s) 361, 366 and/or one or more of A/D converters 369, 370. Accordingly, in some embodiments, photon source 349 and/or 350, photon beam detector(s) 361 and/or 366, A/D converter 369 and/or 370, or a combination thereof, may receive power from a DC battery power source or a low-noise DC power supply for noise reduction.

In some embodiments, power supply 374 can feed photon source 349 and/or photon source 350 to produce at least one low-noise consistent frequency photon beam. In some embodiments, this at least one low-noise consistent frequency photon beam can have a wavelength of about 650 nm. Additionally, generating a photon beam including higher or lower wavelengths can be interchanged or added when specific wavelengths may be indicated. For example, in some embodiments, photon source 349 and/or photon source 350 can include a laser emitting light at a wavelength of about 500 nm.

One or more beam amplitude adjusters 351 can be provided to adjust photon beam intensity. If a single photon source 350 and initial single photon beam is utilized, the beam is passed through optical beam splitter 352. In some embodiments, the optical beam splitter 352 can include one or more mirrors for dividing the single photon beam into two photon beams. One photon beam (the "principal photon beam") is directed towards the cells (i.e., along the left branch of the diagram of FIG. 3) and the other photon beam (the "reference photon beam") towards a separate detector for noise reduction, similar to system 100.

In some embodiments, both photon beams are then directed towards a beam alignment device 353 and a beam alignment device 364, respectively, for aligning the photon beams so that as the photon beams pass through the optics they are centered in the middle of the photon beam detector(s) 361, 366 after passing through the cells/reference medium and the lenses 355, 365. In some embodiments, beam alignment devices 353 and 364 can include a rotating lens.

In some embodiments, system 300 can include a support device (e.g., a table, platform, and/or petri dish) configured to support and/or hold the cells/tissue (together support device and cells (objects) 354, and optionally a WSS) and/or the reference medium (together support device and reference medium 375, and optionally a WSS). (No WSS is illustrated in FIG. 3, but can be used.) In operation, the principal photon beam can pass through the cells/tissue, thereby directly modulating the principal photon beam, and the reference photon beam can pass through the reference medium, thereby directly modulating the reference photon beam. In some embodiments, the support device can include a heater configured to regulate a temperature of the cells/ tissue and/or reference medium. In some embodiments, the cells/tissue (e.g., object(s)) themselves can be provided in a matrix/medium and placed on a table (optionally in a petri dish) so a photon beam can pass by or through them. In some embodiments, an optional low-noise power supply and stepping motor mechanism may be utilized for moving the cells into different positions within a photon beam. In some embodiments, both the cells/tissue and the reference medium are held in a petri dish that uses a WSS to sit on top of a growth medium (e.g., of support device and cells 354) and the reference medium (which can, in some cases, be the growth medium held in the same or a separate petri dish). A support device as described herein may be considered to include a petri dish, which can include a WSS.

In some embodiments, the photon beams then enter objective lens 355 and objective lens 365. In some embodiments, the principal photon beam can be split into two or more photon beams (e.g., three photon beams) with optical beam splitter(s) 356, for example. In some embodiments, an optical splitter compensation module 373 can be included to allow the resultant split photon beams of the principal photon beam and the reference photon beam to be equal in intensity. The three photon beams of the principal photon beam can then enter optical eye piece(s) 358, a camera 357 (e.g., a low-light camera) used for positioning, and photon beam detector(s) 361. In some embodiments, camera 357 can also be connected to a computer 359 to provide the output of camera 357 to a monitor 360 for display.

Photon beam detectors 361 and/or 366 can include a single integrated single light detector or multiple pixel detector and/or an appropriate CCD or QCMOS image sensor. In some embodiments, the photon beam detectors 361 and/or 366 can be low-noise detectors, and it should be understood that any low-noise light detector system(s) could be utilized. In some embodiments, photon beam detector(s) 361 and 366 and amplifiers 362 and 367 can be the same as or similar to detector(s) and amplifier(s) 106 of FIG. 1. The outputs of photon beam detector(s) 361 and 366 can also enter amplifiers 362 and 367 and bias and gain adjusters 363 and 368, which can assist with DC offset and signal level. In some embodiments, a DC offset and bias can be adjusted to align signals from the principle and reference photon beams, for example, using techniques described in the above patents incorporated by reference herein.

In some embodiments, system 300 can include an optional auxiliary signal injection element to assist with noise reduction for the bias and gain adjusters 363 and 368 and amplifiers 362 and 367. In such embodiments, system 300 can include a switch to turn the signal injection element on and off.

In some embodiments, the analog signal of the principal photon beam modulated by the cell/tissue movement enters an A/D converter 370. Similarly, the analog signal of the reference photon beam modulated by the reference medium enters an A/D converter 369. (In some embodiments, a single A/D converter may be used with multiplexing.) In some embodiments, A/D converter 370 and/or A/D converter 369 can be the same as or similar to A/D converters 108P, 108R and/or 208P, 208R described with respect to FIGS. 1 and 2. In some embodiments, the data from the two A/D converters is synchronous in nature, as described above with respect to FIGS. 1 and 2. The resulting digital signals are then received by a computer 371 that is configured to acquire the digital signal data, store the digital signal data, perform algorithmic CPNR techniques and the like on the digital signal data, and perform digital measuring of the signals to create partial and event information. The computer 371 can also include a memory (e.g., non-volatile data storage, such as an HDD or solid-state digital storage unit) for storing the digital signal data and the characterization results long term.

In some embodiments, signal analysis and CPNR software 372 can be run by computer 371 to generate partial and event data, organize digital signal data into a PMM or other time/frequency/amplitude framework for creating 3D matrix outputs and/or histograms, and/or characterization data based on filtering of the events created from the digital signal data stream. For example, moving cells create at times harmonics that can be measured by the PMM utilizing the harmonic domain. The PMM can be implemented in hardware, software, or a combination of both. In some embodiments, the creation of PMMs and/or use of PMMs in CPNR can be performed by a software module that is part of signal analysis and CPNR software 372. The characterization data (e.g., that characterizes vibrational spectra of cells, a cell, and/or sub-components of a cell) can then be provided in multiple data formats as an output 376 that can be received by other devices and can be displayed on a computer monitor. In some embodiments, a time code module can be included in system 300 for tracking an optional movie and/or video (e.g., captured using camera 357), stimuli to cells/tissue, and the characterization data simultaneously.

Figure 4A:
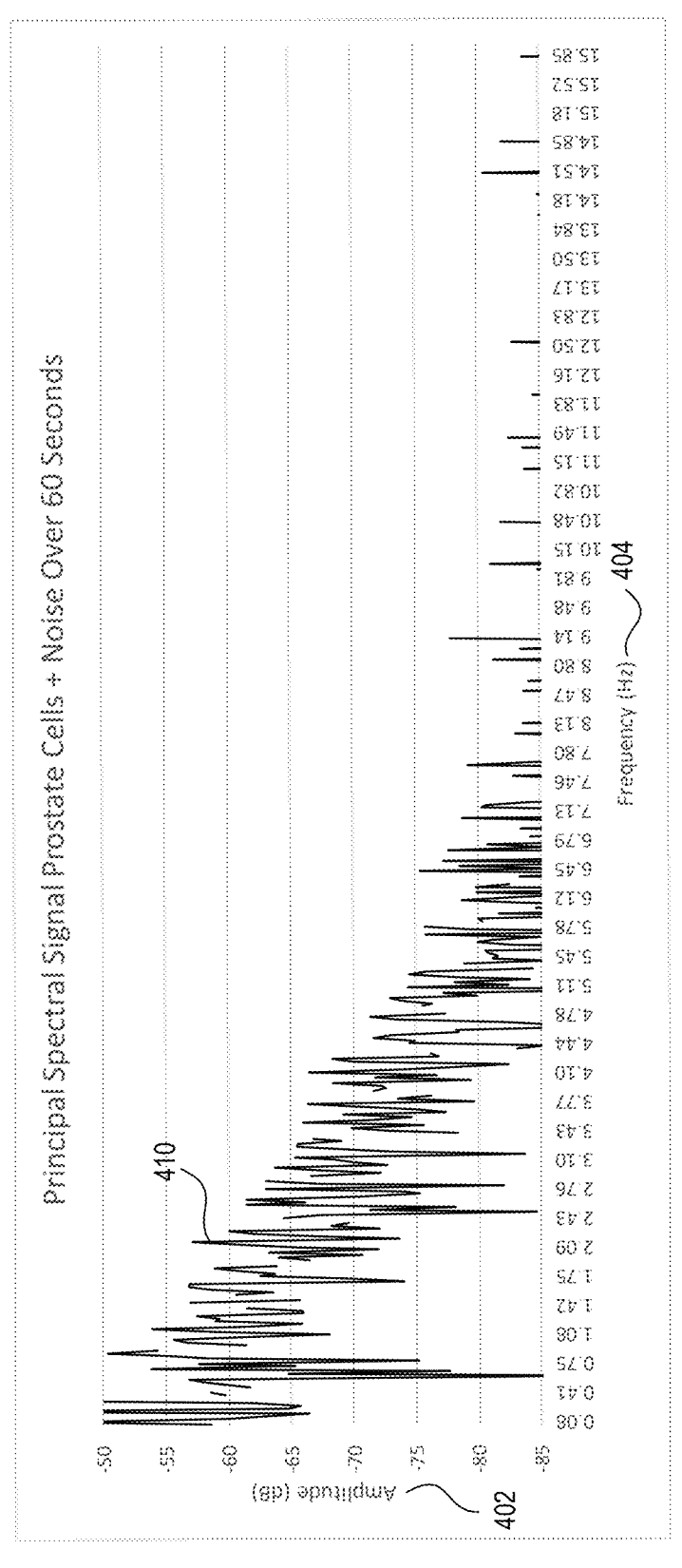
FIG. 4A illustrates an amplitude-frequency graph of principal signal path data, according to some embodiments.
Figure 4B:
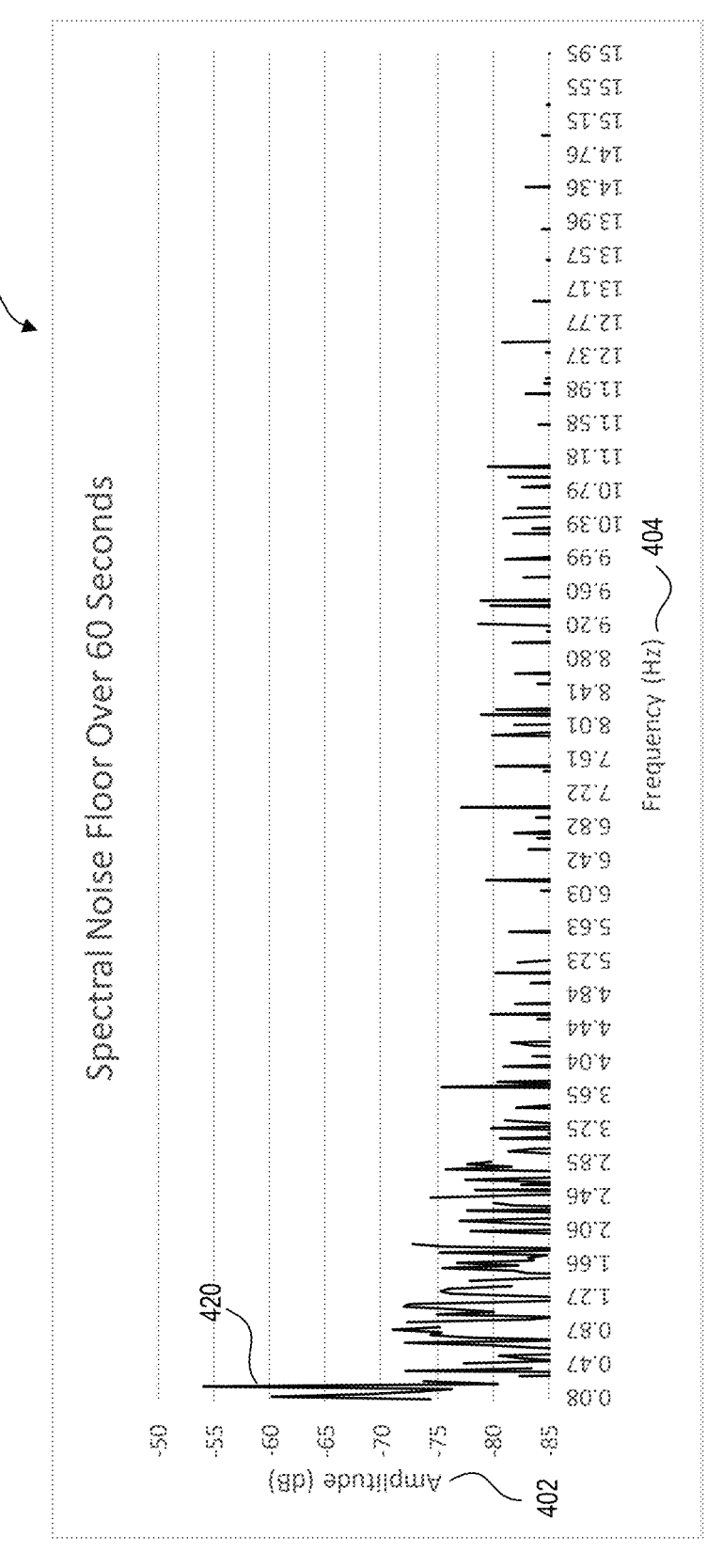
FIG. 4B illustrates an amplitude-frequency graph of reference signal path data, according to some embodiments.
Figure 4C:
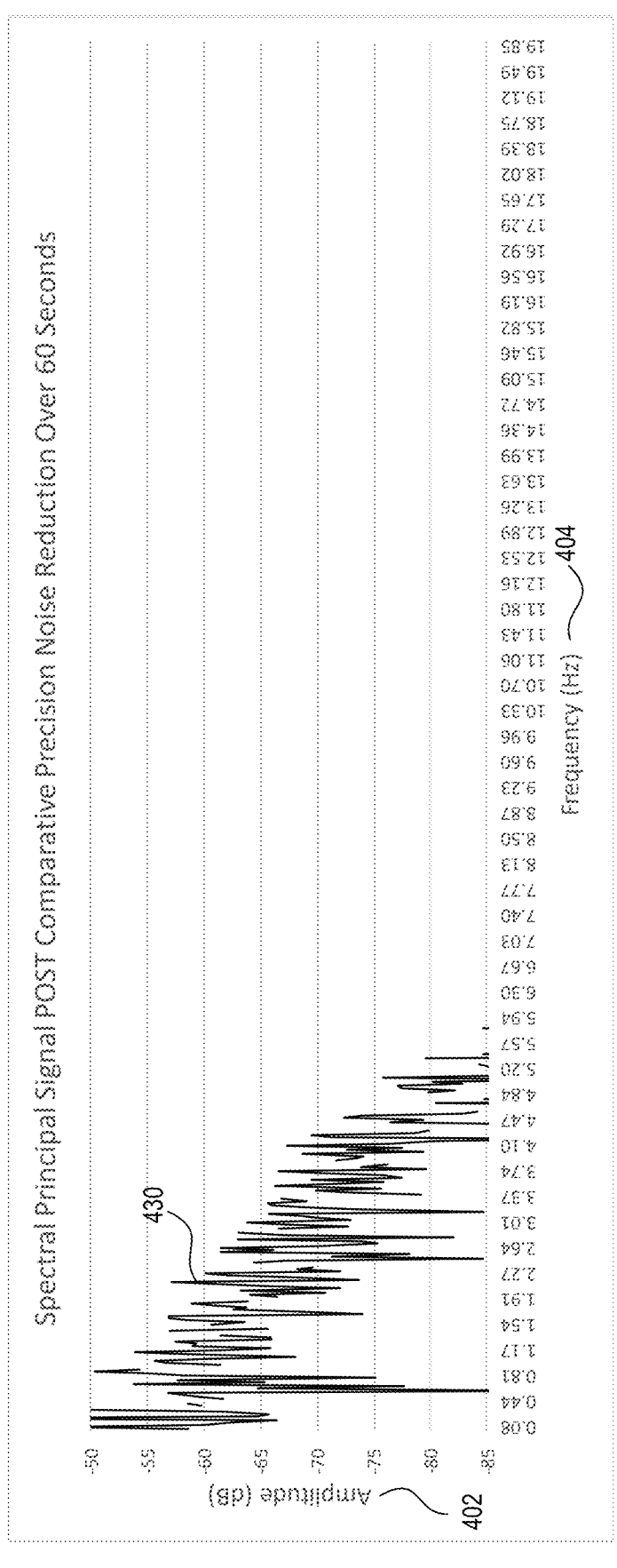
FIG. 4C illustrates an amplitude-frequency graph of the principal signal path data of FIG. 4A post comparative precision noise reduction (CPNR), according to some embodiments.

FIGS. 4A-4C illustrate histogram type amplitude-frequency graphs of principal signal path data, reference signal path data, and principle signal path data post CPNR, respectively, according to some embodiments. For each of FIGS. 4A-4C, the data shown is for a range of 0.1 Hz to 20 Hz with amplitude ranges of −85 dB to −50 dB. Amplitude 402 values shown represent the sum value of amplitudes for each 0.03 Hz-wide frequency 404 bin over 60 seconds of data gathering. Signal 410 represents digital signal data from the principal signal path received from an A/D converter, as described with respect to FIGS. 1-3. Signal 420 represents digital signal data from the reference signal path received from an A/D converter, as described with respect to FIGS. 1-3. Signal 430 represents digital signal data from the principal signal path with noise removed via CPNR. A comparison of FIGS. 4C and 4A shows that a significant total amplitude of noise events has been removed from the principal signal path data by CPNR in FIG. 4C.

Figure 5A:
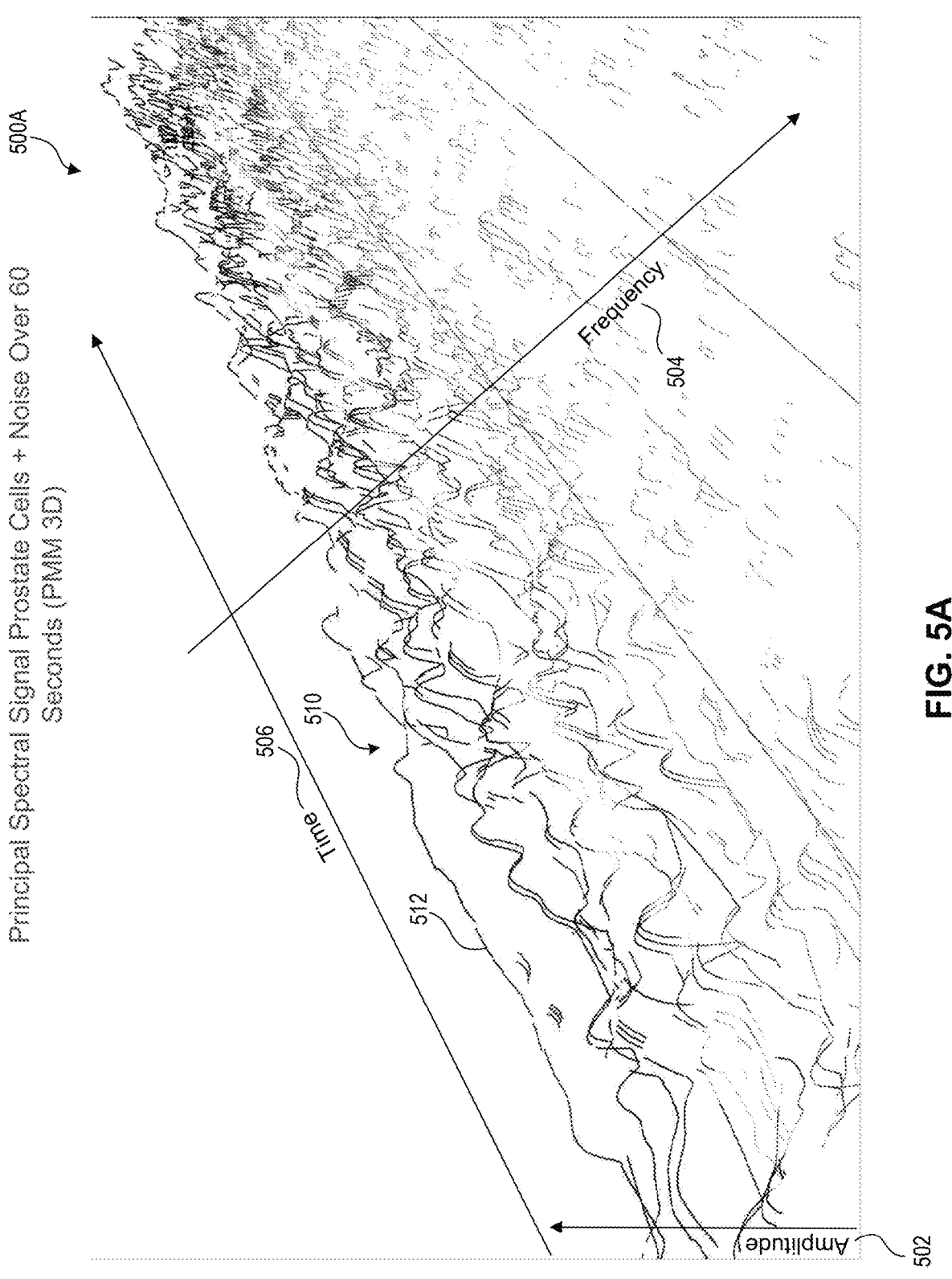
FIG. 5A illustrates an amplitude-frequency-time 3D graph of principal signal path data, according to some embodiments.
Figure 5B:
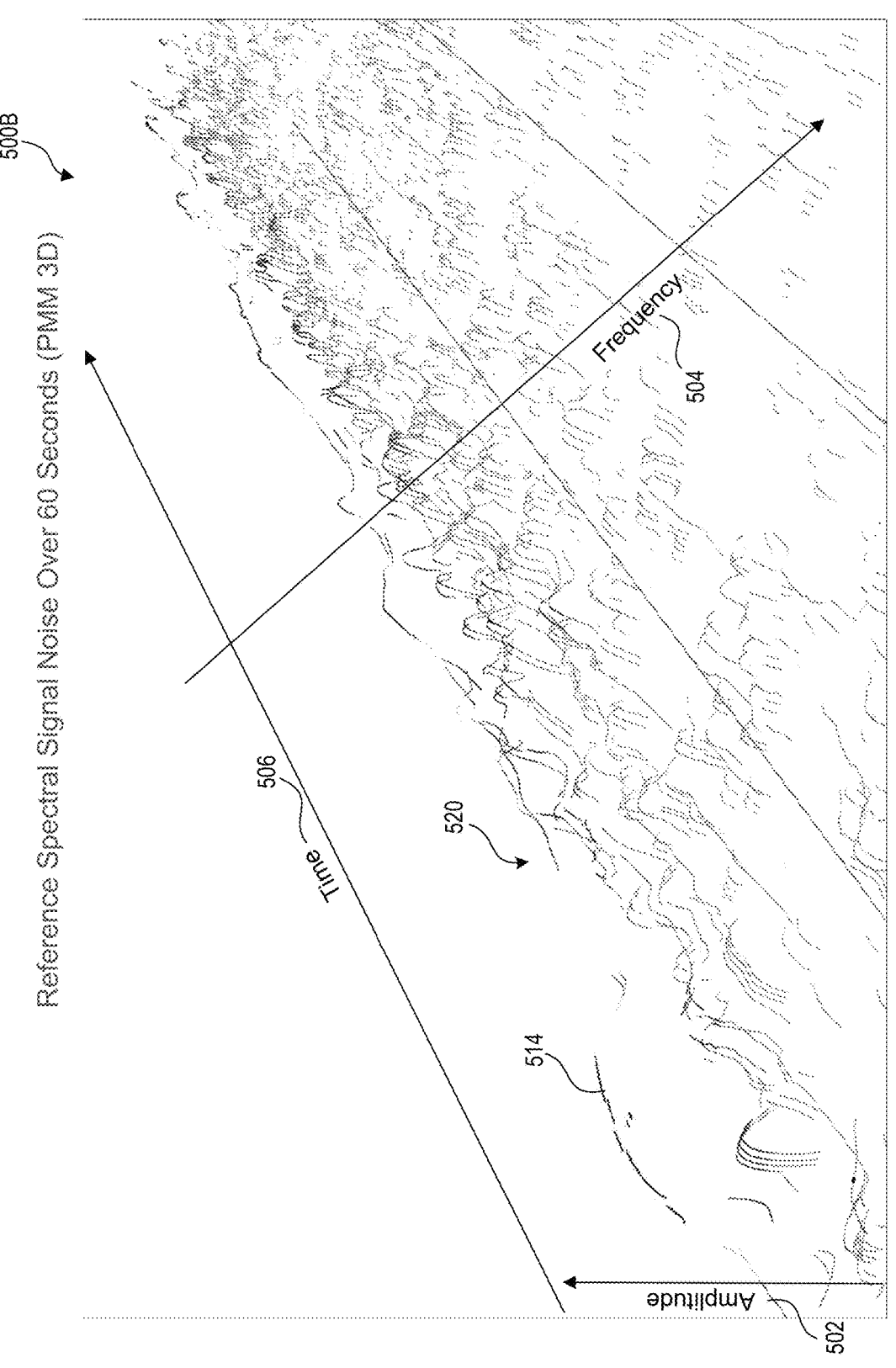
FIG. 5B illustrates an amplitude-frequency-time 3D graph of reference signal path data, according to some embodiments.
Figure 5C:
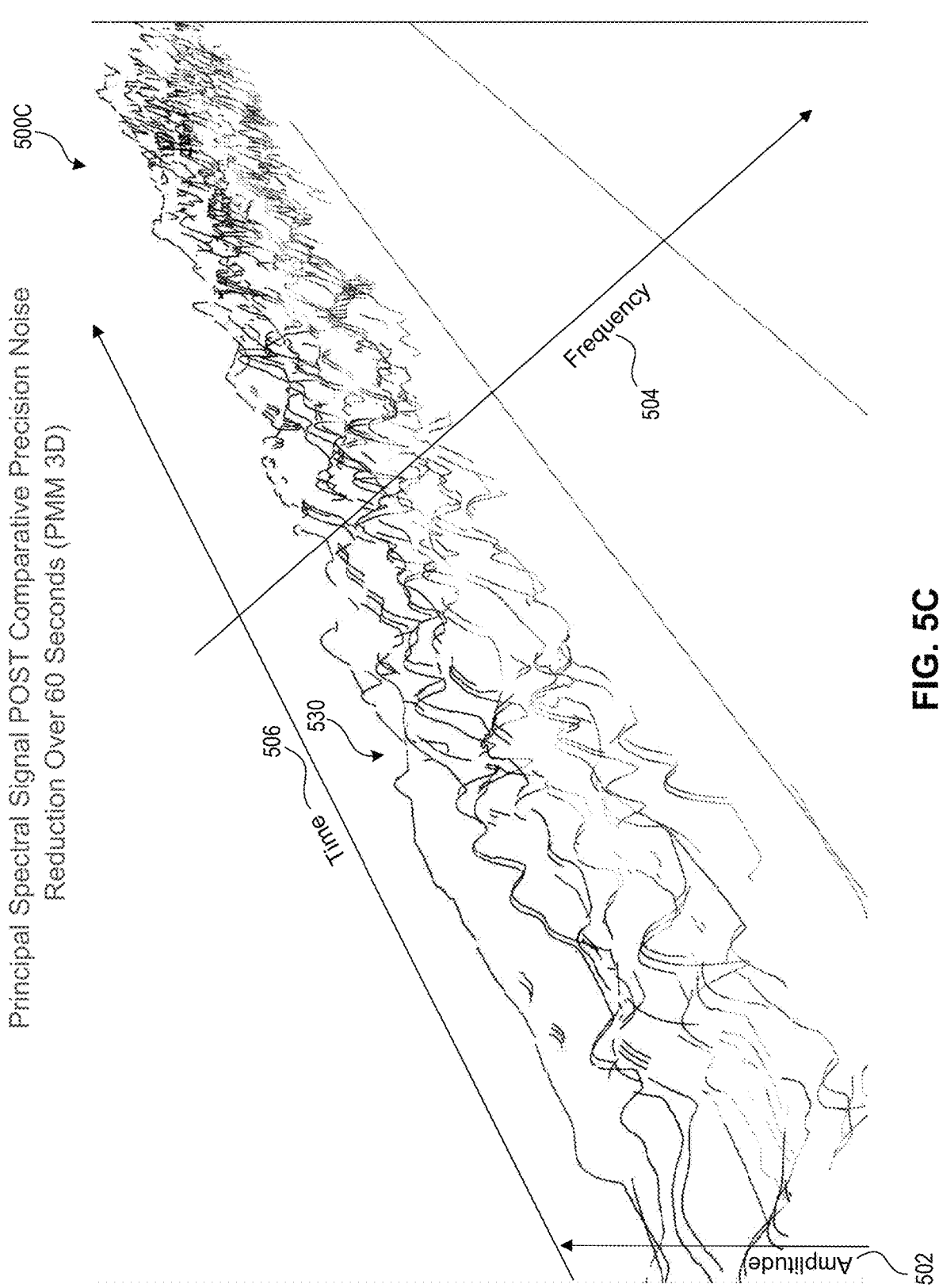
FIG. 5C illustrates an amplitude-frequency-time 3D graph of the principal signal path data of FIG. 5A post CPNR, according to some embodiments.

FIGS. 5A-5C illustrate PMM type amplitude-frequency-time graphs of principal signal path data, reference signal path data, and principal signal path data post CPNR, respectively, according to some embodiments. Signal 510 (all lines in FIG. 5A) represents digital signal data from the principal signal path received via an A/D converter, as described with respect to FIGS. 1-3, over 60 seconds and characterized using a PMM. Signal 520 represents digital signal data from the reference signal path received via an A/D converter, as described with respect to FIGS. 1-3, over 60 seconds and characterized using a PMM. Signal 530 represents digital signal data from the principal signal path with noise removed via CPNR, characterized using a PMM.

FIGS. 5A-5C illustrate example events, for example, an event 512. In some embodiments, event 512 can be a continuous line of data as displayed on a 3D PMM representation such as that shown in FIG. 5A. However, an event can be any pattern of data quantifiable in time, frequency, and/or amplitude that can be identified from the principal or reference digital representations. As shown in FIG. 5A, an event often exists within a narrow band of frequencies.

A comparison of FIGS. 5C and 5A shows that a significant number of noise events have been identified and removed from the principal signal path data by CPNR in FIG. 5C.

Figure 6A:
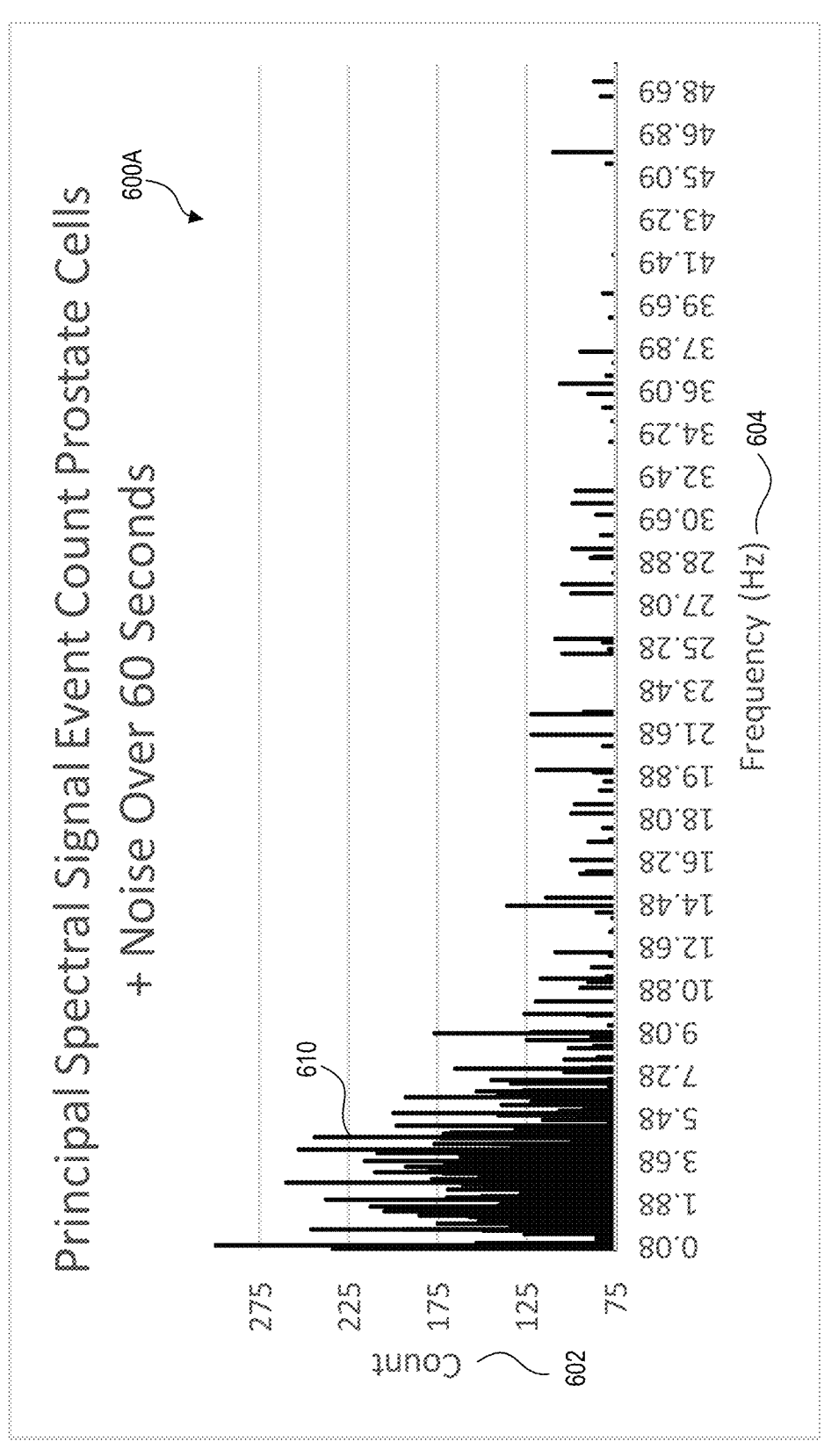
FIG. 6A illustrates an event count-frequency graph of principal signal path data, according to some embodiments.
Figure 6B:
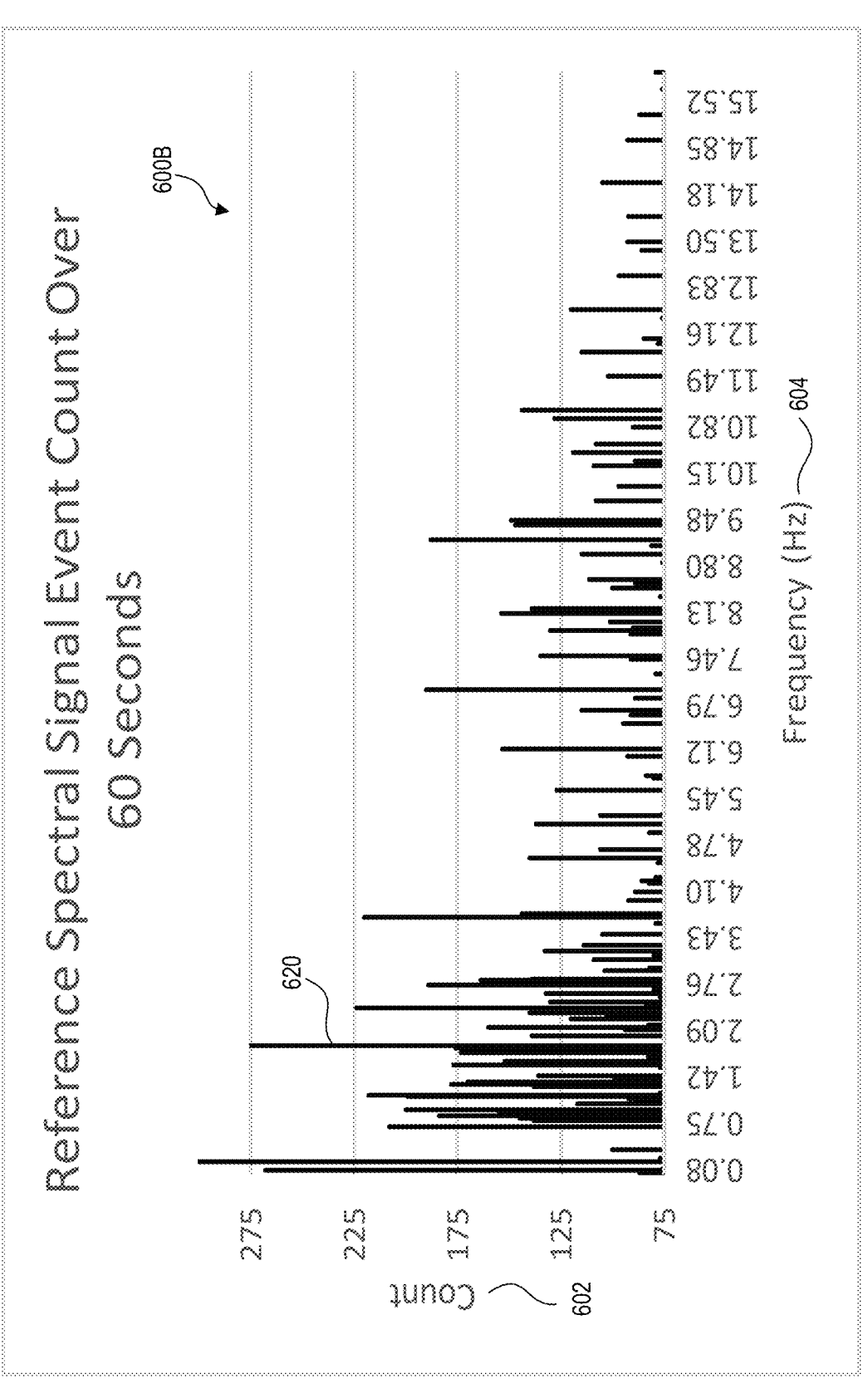
FIG. 6B illustrates an event count-frequency graph of reference signal path data, according to some embodiments.
Figure 6C:
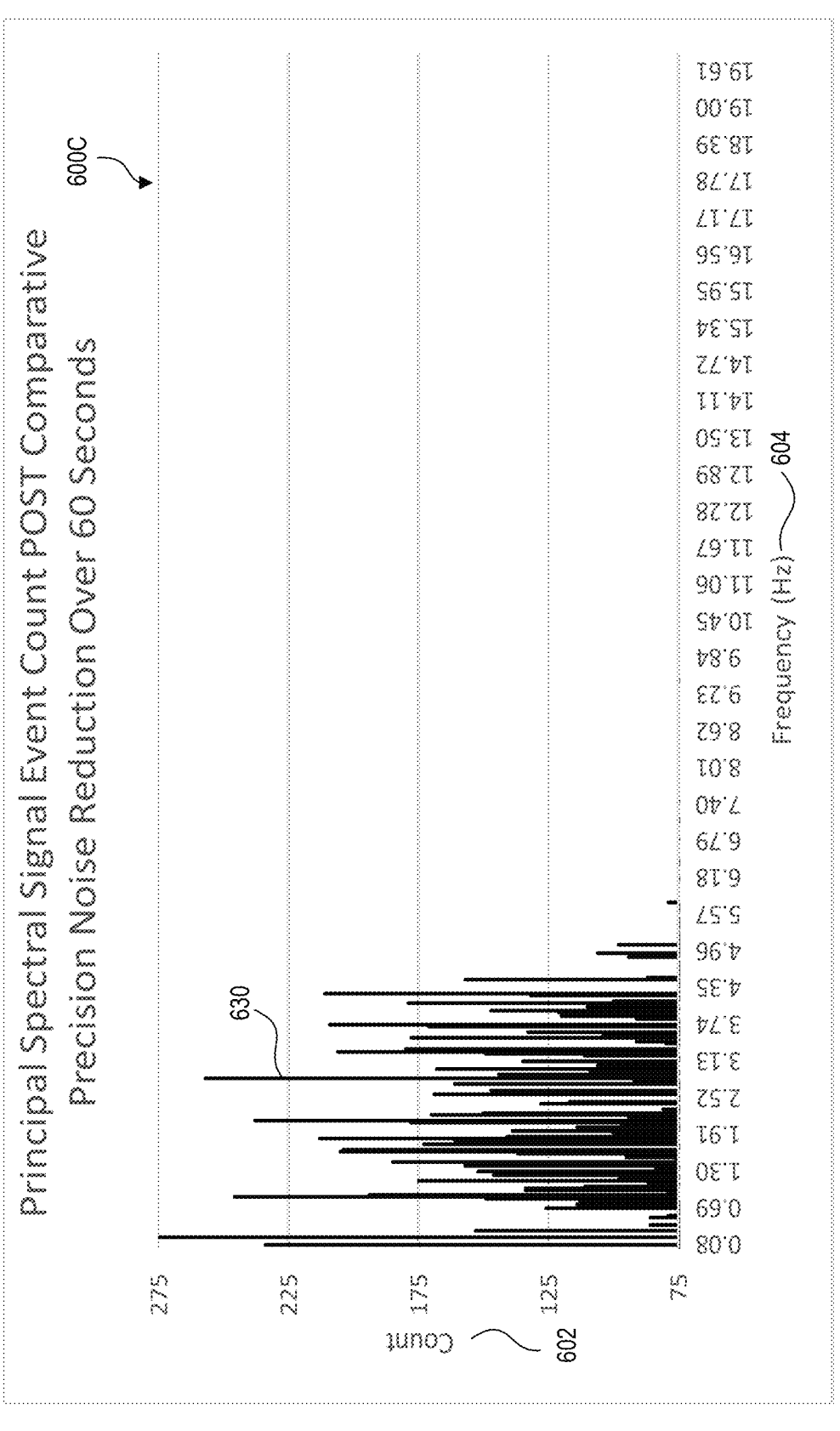
FIG. 6C illustrates an event count-frequency graph of the principal signal path data of FIG. 6A post CPNR, according to some embodiments.

FIGS. 6A-6C illustrate histogram type event count-frequency graphs (e.g., histograms) of principal signal path data, reference signal path data, and principal signal path data post CPNR, respectively according to some embodiments. Signal 610 represents digital signal data from the principal signal path received via an A/D converter, as described with respect to FIGS. 1-3, over 60 seconds. Signal 620 represents digital signal data from the reference signal path received via an A/D converter, as described with respect to FIGS. 1-3, over 60 seconds. Signal 630 represents digital signal data from the principal signal path with noise removed via CPNR.

As shown in FIGS. 6A-6C, the event count 602 can be the number of events detected within a band of frequencies 604. A comparison of FIGS. 6C and 6A shows that a significant number of noise events have been identified and removed from the principal signal path data by CPNR in FIG. 6C.

Figure 7A:
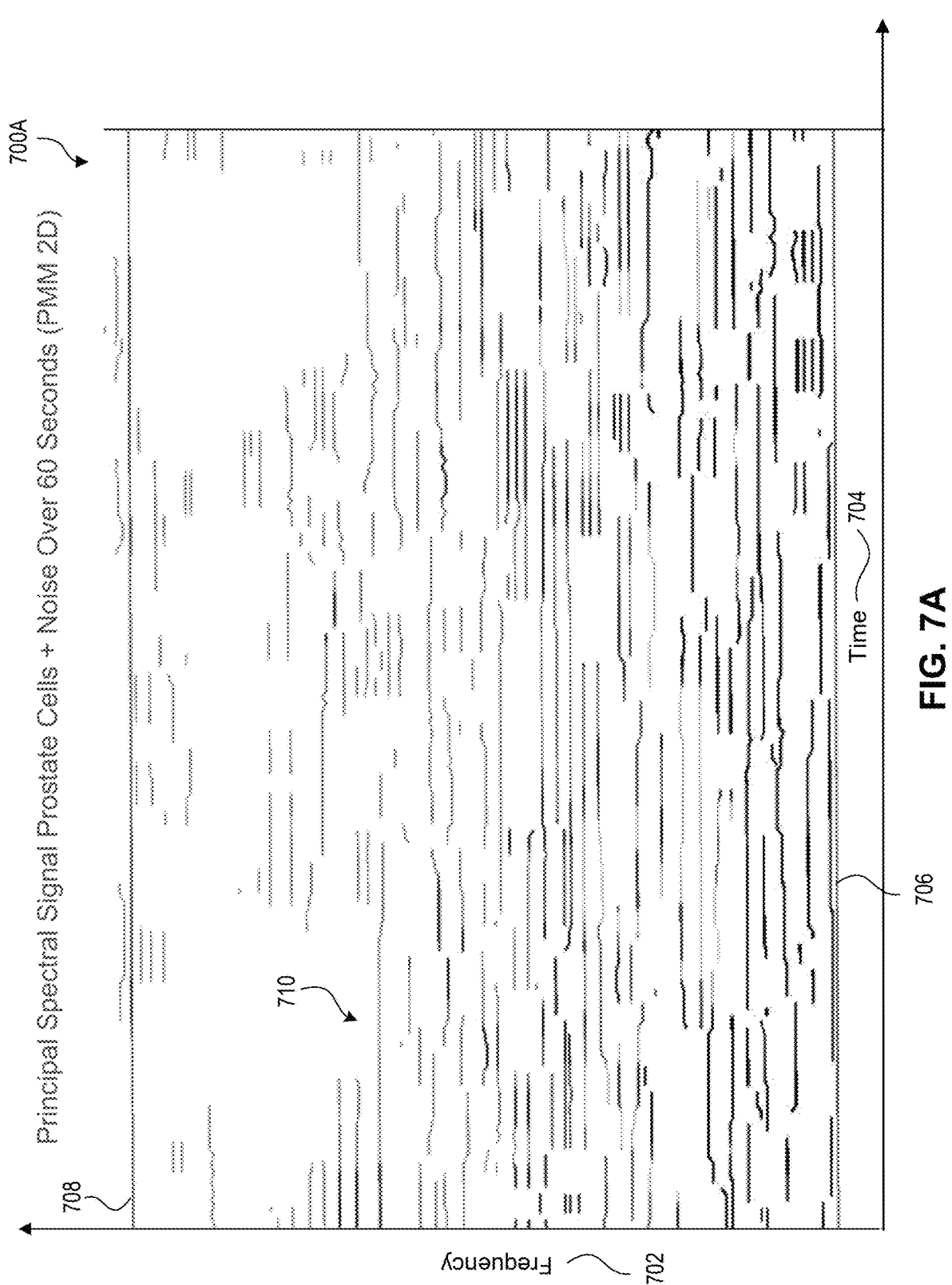
FIG. 7A illustrates a frequency-time graph of 2D principal signal path data, according to some embodiments.
Figure 7B:
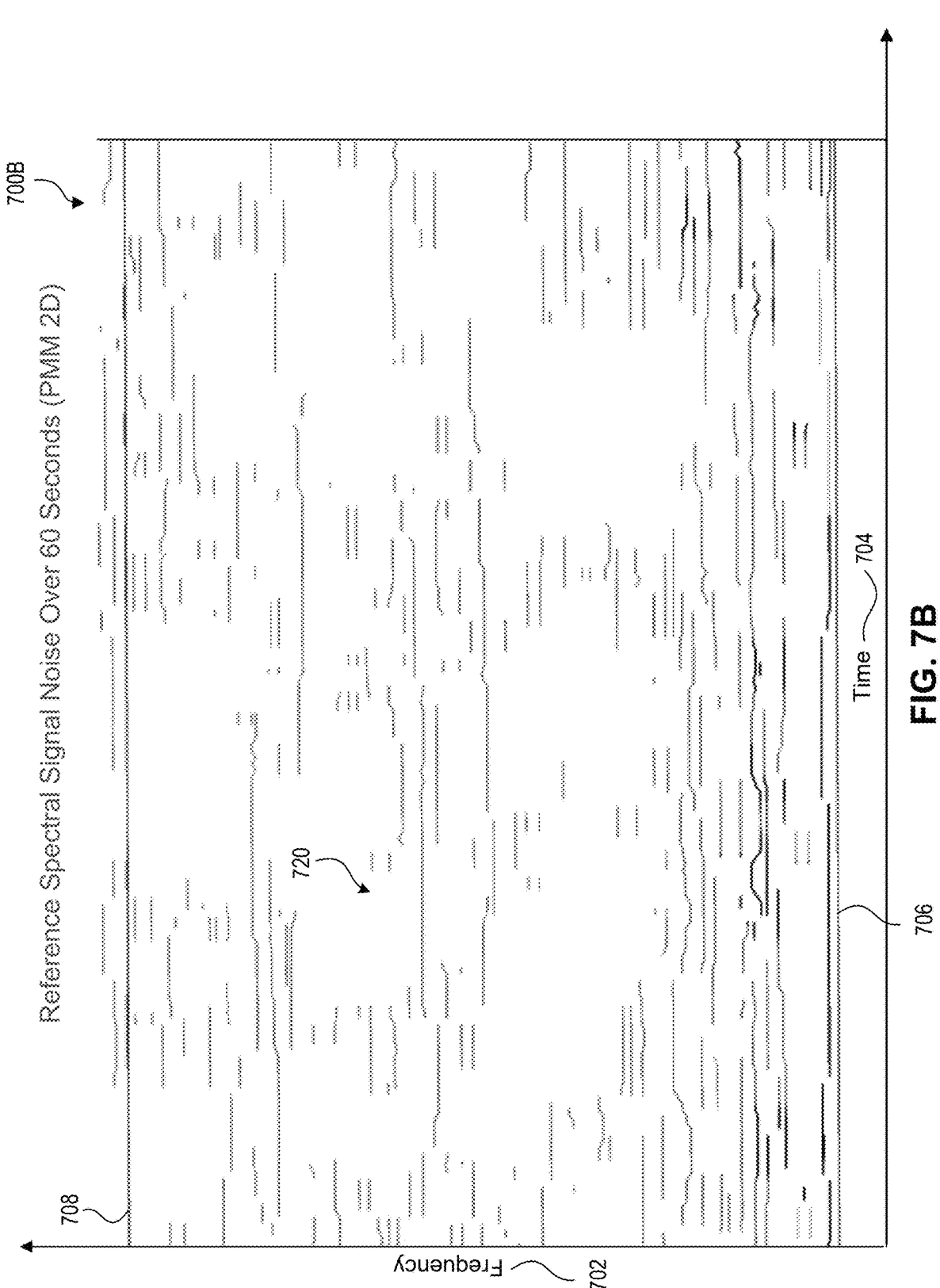
FIG. 7B illustrates a frequency-time graph of 2D reference signal path data, according to some embodiments.
Figure 7C:
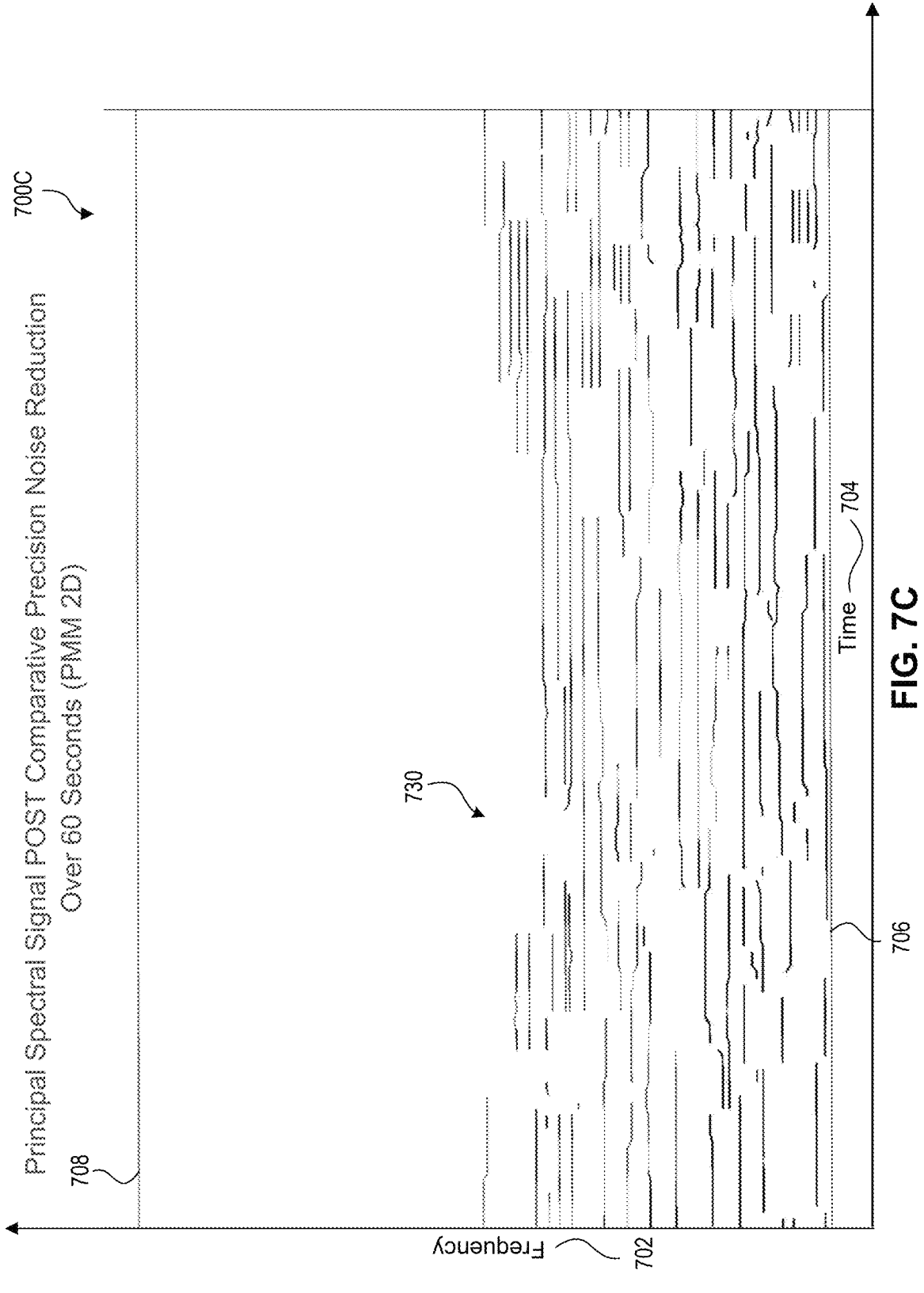
FIG. 7C illustrates a frequency-time graph of the 2D principal signal path data of FIG. 7A post CPNR, according to some embodiments.

FIGS. 7A-7C illustrate 2D PMM type frequency-time graphs of principal signal path data, reference signal path data, and principal signal path data post CPNR, respectively, according to some embodiments. Signal 710 (all lines in FIG. 7A) represents digital signal data from the principal signal path received via an A/D converter, as described with respect to FIGS. 1-3, over 60 seconds and characterized using a PMM. Signal 720 represents digital signal data from the reference signal path received via an A/D converter, as described with respect to FIGS. 1-3, over 60 seconds and characterized using a PMM. Signal 730 represents digital signal data from the principal signal path with noise removed via CPNR, characterized using a PMM. In some embodiments, first and second indicators 706, 708 can indicate a frequency range, for example, a frequency range from about 0 Hz to about 20 Hz.

A comparison of FIGS. 7C and 7A shows that a significant number of noise events have been identified and removed from the principal signal path data by CPNR in FIG. 7C.

Exemplary CPNR Techniques

Example methods for identifying and removing noise events using CPNR will now be described.

FIG. 8 is a flow chart depicting a method 800 that can be carried out in line with the present disclosure. One or more of the operations in the method depicted by FIG. 8 could be carried out by one or more entities, including, without limitation, processor(s) 110, processor(s) 210, computer 371, signal analysis and CPNR software 372, or other server or cloud-based server processing systems and/or one or more entities operating on behalf of or in cooperation with these or other entities. Any such entity could embody a computing system, such as a programmed processing unit or the like, configured to carry out one or more of the method operations. Further, a non-transitory data storage (e.g., disc storage, flash storage, or other computer readable medium) could have stored thereon instructions executable by a processing unit to carry out the various depicted operations.

Unless stated otherwise, the steps of method 800 need not be performed in the order set forth herein. Additionally, unless specified otherwise, the steps of method 800 need not be performed sequentially. The steps may be performed in a different order or simultaneously. Further, method 800 may not include all the steps illustrated. For example, in some embodiments, method 800 may not include steps 802-806, and can instead include generating a single photon beam and detecting the photon beam and vibrations measured by a sensor (e.g., an accelerometer) as described with respect to FIG. 2.

Step 802 can include generating a first photon beam and a second photon beam (e.g., using photon source 102P and 102R or a photon source and beam splitter 103).

Step 804 can include passing the first photon beam through an object (e.g., cells/living tissue/object, and optionally a WSS) and a second photon beam through a reference medium (and optionally a WSS). In some embodiments, passing the first and second photon beams through the object and the reference medium can directly modulate the first and second photon beams.

Step 806 can include detecting the modulated first and second photon beams (e.g., using detector(s) and amplifier(s) 106P, 106R). In some embodiments, step 806 can also include producing first and second analog signals representative of the resultant vibrational spectra of the object and the resultant noise spectra of the reference medium. As noted above, the first analog signal representative of the resultant vibrational spectra of the object can also include some noise.

Step 808 can include converting the first and second analog signals into first and second digital representations, respectively (e.g., using A/D converter(s) 108P, 108R).

Step 810 can include defining one or more reference events. In some embodiments, step 810 can include defining one or more reference events from the second digital representation (i.e., from data from the reference path discussed herein). In some embodiments, each of the one or more reference events can include a time characteristic, a frequency characteristic, and an amplitude characteristic. In some embodiments, the time characteristic, frequency characteristic, and amplitude characteristic can be determined by signal analysis module 112, 212 and/or signal analysis and CPNR software 372. In some embodiments, defining the one or more reference events in step 810 can include one or more of mapping the second digital representation to one or more partials, each partial representing an amplitude specified over a specific frequency range and time period, and chaining the one or more partials into the one or more reference events. In some embodiments, the mapping and chaining can be performed using a precision measuring matrix (PMM).

In some embodiments, defining one or more reference events in step 810 can include categorizing the one or more reference events into at least one domain. In some embodiments, the at least one domain can include a time domain, a frequency domain, an amplitude domain, a harmonic domain, a partial chain domain, a memory domain, a non-random domain, or a combination thereof. In some embodiments, domain categorization can be performed by signal analysis module 212. Domain categorization can be performed as described in U.S. Pat. No. 9,279,839 B2, issued Mar. 8, 2016 and titled "Domain Identification and Separation for Precision Measurement of Waveforms," the disclosure of which is incorporated by reference herein in its entirety.

Step 812 can include identifying one or more matching events. In some embodiments, step 812 can include identifying one or more matching events from the first digital representation (i.e., from data from the principal path discussed herein). In some embodiments, each of the one or more matching events can correspond to a reference event of the one or more reference events. In some embodiments, to identify the one or more matching events, events from the first digital representation can be defined and time characteristics, frequency characteristics, and amplitude characteristics for the events from the first digital representation can be determined by signal analysis module 112, 212 and/or signal analysis and CPNR software 372 to enable a comparison to the one or more reference events.

In some embodiments, the time characteristic of a reference event can include a start time of the reference event, an end time of the reference event, a duration of the reference event, an absolute start time of the reference event, or a combination thereof. In some embodiments, identifying the one or more matching events can include identifying a matching event including a matching time characteristic, the matching time characteristic including a start time within a predetermined range from the start time of the reference event, an end time within a predetermined range from the end time of the reference event, a duration within a predetermined range from the duration of the reference event, an absolute start time within a predetermined range from the absolute start time of the reference event, or a combination thereof.

The "predetermined ranges" can be defined in a number of ways. For example, in some embodiments, the predetermined range can be defined as a delta from a value of a time characteristic. As a non-limiting example, should the time characteristic of the reference event include a start time of the reference event, the matching time characteristic of the matching event can include a start time within 0.5 seconds, within 0.4 seconds, within 0.3 seconds, within 0.2 seconds, within 0.1 seconds, within 0.05 seconds, within 0.025 seconds, within 0.01 seconds, etc., however the delta value is defined within the CPNR algorithm. Additionally or alternatively, in some embodiments, the delta can be defined as a percentage difference from a value of a time characteristic. As a non-limiting example, should the time characteristic of the reference event include an end time of the reference event, the matching time characteristic of the matching event can include an end time within 50%, within 40%, within 30%, within 20%, within 10%, within 5%, within 3%, or within 1% of the end time of the reference event, etc., however the delta value is defined within the CPNR algorithm. Additionally or alternatively, in some embodiments, the delta can be defined based on a percentage range of a value of a time characteristic. As a non-limiting example, should the time characteristic of the reference event include a duration of the reference event, the matching time characteristic of the matching event can include a duration within 50% to 150%, within 60% to 140%, within 70% to 130%, within 80% to 120%, within 90% to 110%, within 95% to 105%, or within 98% to 102% of the duration of the reference event, etc., however the delta value is defined within the CPNR algorithm.

Any one, any combination, or all of the example parameters provided above can be included in a time characteristic (e.g., start time, end time, duration, absolute start time). Therefore, in some aspects, identifying the matching event can include confirming that multiple time characteristic values each fall within a predetermined range of a corresponding time characteristic value (e.g., start time compared to start time, end time compared to end time, duration compared to duration, etc.).

The "absolute start time" of an event should be understood to be the start time according to a master clock (e.g., clock 120P) that is independent from or is used to synchronize separate clocks used to timestamp data from separate signal paths (e.g., clocks 120P and 120R). Accordingly, the "absolute start time" represents a global time that has been measured through either synchronizing clocks used to timestamp data from separate signal paths or adjusting timestamps post-data collection to reflect a global time measured by a master clock.

In some embodiments, method 800 can include categorizing the reference event as a transient reference event (e.g., using signal analysis module 212). In such embodiments, the matching time characteristic can include the absolute start time within a predetermined range from the absolute start time of the reference event. A transient event can be an event that is of short duration and/or high intensity (amplitude). In some embodiments, signal analysis module 212 can categorize such an event by determining an event has a duration below a threshold duration and/or an amplitude above a threshold amplitude. A transient reference event can be more likely to be a noise event caused by external factors (e.g., a support device moving, etc.) such that a matching event is more likely to be identified at about the same absolute time (e.g., absolute start time). Accordingly, the CPNR algorithm can select, based on the categorization, that the time characteristic of the reference event includes the absolute start time of the reference event, excludes other time characteristic values during comparison, and/or that events from the first digital representation that are around the same absolute start time are compared to the reference event before other events.

In some embodiments, method 800 can include categorizing the reference event as a static reference event. In such embodiments, the matching time characteristic can include the duration within a predetermined range from the duration of the reference event. A static event can be an event that is of longer duration and/or low intensity (amplitude). In some embodiments, signal analysis module 212 can categorize such an event by determining an event has a duration above a threshold duration and/or an amplitude below a threshold amplitude. A static reference event can be more likely to be a noise event caused by internal factors (e.g., Gaussian noise from electronic components and/or thermal radiation) such that a matching event is more likely to be identified based on having the same or similar duration, but not necessarily the same absolute start time. Accordingly, the CPNR algorithm can select, based on the categorization, that the time characteristic of the reference event includes the duration of the reference event, excludes other time characteristic values during comparison, and/or that events from the first digital representation that are around the duration are compared to the reference event before other events.

In some embodiments, the frequency characteristic of a reference event can include a start frequency of the reference event, an end frequency of the reference event, a lower frequency of the reference event, an upper frequency of the reference event, a delta between the lower and upper frequencies of the reference event, or a combination thereof. In some embodiments, identifying the one or more matching events can include identifying a matching event including a matching frequency characteristic, the matching frequency characteristic including a start frequency within a predetermined range from the start frequency of the reference event, an end frequency within a predetermined range from the end frequency of the reference event, a lower frequency within a predetermined range from the lower frequency of the reference event, an upper frequency within a predetermined range from the upper frequency of the reference event, a delta between the lower and upper frequencies within a predetermined range from the delta between the lower and upper frequencies of the reference event, or a combination thereof.

The "predetermined ranges" for the frequency characteristic can be defined the same way as the predetermined ranges for the time characteristic, as discussed above. Any one, any combination, or all of the example parameters provided above can be included in a frequency characteristic (e.g., start frequency, end frequency, lower frequency, upper frequency, delta between the lower and upper frequencies). Therefore, in some cases, identifying the matching event can include confirming that multiple frequency characteristic values each fall within a predetermined range of a corresponding frequency characteristic value (e.g., start frequency compared to start frequency, end frequency compared to end frequency, etc.).

In some embodiments, the amplitude characteristic of a reference event can include a start amplitude of the reference event, an end amplitude of the reference event, a lower amplitude of the reference event, an upper amplitude of the reference event, a delta between the lower and upper amplitudes of the reference event, or a combination thereof. In some embodiments, identifying the one or more matching events can include identifying a matching event including a matching amplitude characteristic, the matching amplitude characteristic comprising a start amplitude within a predetermined range from the start amplitude of the reference event, an end amplitude within a predetermined range from the end amplitude of the reference event, a lower amplitude within a predetermined range from the lower amplitude of the reference event, an upper amplitude within a predetermined range from the upper amplitude of the reference event, a delta between the lower and upper amplitudes within a predetermined range from the delta between the lower and upper amplitudes of the reference event, or a combination thereof.

The "predetermined ranges" for the amplitude characteristic can be defined the same way as the predetermined ranges for the time characteristic, as discussed above.

Any one, any combination, or all of the example parameters provided above can be included in an amplitude characteristic (e.g., start amplitude, end amplitude, lower amplitude, upper amplitude, delta between the lower and upper amplitudes). Therefore, in some cases, identifying the matching event can include confirming that multiple amplitude characteristic values each fall within a predetermined range of a corresponding amplitude characteristic value (e.g., start amplitude compared to start amplitude, end amplitude compared to end amplitude, etc.).

In some embodiments, defining one or more reference events in step 810 can include categorizing the one or more reference events into at least one domain. In some embodiments, the at least one domain can include a time domain, a frequency domain, an amplitude domain, a harmonic domain, a partial chain domain, a memory domain, a non-random domain, or a combination thereof. In some embodiments, domain categorization can be performed by signal analysis module 212. Domain categorization can be performed as described in U.S. Pat. No. 9,279,839 B2, issued Mar. 8, 2016 and titled "Domain Identification and Separation for Precision Measurement of Waveforms," the disclosure of which is incorporated by reference herein in its entirety. In some embodiments, identifying the one or more matching events in step 812 can include comparing a categorized reference event to an event from the first digital representation that shares at least one domain with the categorized reference event, prior to identifying the event as a matching event. In some embodiments, the CPNR algorithm can compare events that share at least one domain to reduce processing costs associated with comparing a reference event to all events from the first digital representation. In some embodiments, the CPNR algorithm can compare a reference event to events from the first digital representation that share the most domains with the reference event, followed by events from the first digital representation that share fewer domains with the reference event, until a matching event is founds or all events have been compared.

In comparing an event from the first digital representation (i.e., from the principal signal path) to a reference event from the second digital representation (i.e., from the reference signal path) to determine whether a matching event is identified, any one, any combination, or all of time characteristics, frequency characteristics, and amplitude characteristics can be compared. Accordingly, in some embodiments, the process of comparison and identifying the one or more matching events can be explained as trying to find a line in FIG. 5A (e.g., event 512) that has a similar shape, length, start point, end point, and/or position as a line in FIG. 5B (e.g., event 514). If the shape, length, start point, end point, and/or position is similar enough, as defined by the predetermined ranges discussed above, the line (i.e., event) is identified as a noise event and can be removed from the digital representation of the principal signal shown in FIG. 5A. Similarly, if only frequency and time characteristics are considered in the comparison, the process of comparison and identifying the one or more matching events can be explained as trying to find a line in FIG. 7A that has a similar shape, length, start point, end point, and/or position as a line in FIG. 7B. If the shape, length, start point, end point, and/or position is similar enough, as defined by the predetermined ranges discussed above, the line (i.e., event) is identified as a noise event and can be removed from the digital representation of the principal signal shown in FIG. 7A.

Step 814 can include removing the one or more matching events. In some embodiments, step 814 can include removing the one or more matching events from the first digital representation, thereby outputting and/or storing a noise-filtered digital representation of the vibrational spectra of the object with little to no noise (step 816). In some embodiments, the one or more matching events need not be removed directly from the first digital representation to be removed, but the first digital representation and data on the matching events may be used to produce the noise-filtered digital representation of the vibrational spectra of the object with little to no noise (e.g., all events of the first digital representation except the matching events can be moved to a different noise-filtered output file).

In some embodiments, the reference medium can include a reference object. Accordingly, in some embodiments, method 800 can include comparing a vibrational spectra of a reference object of the reference medium to the vibrational spectra of the object such that the noise-filtered digital representation comprises a noise-filtered digital representation of differences between the vibrational spectra of the object and the vibrational spectra of the reference object. In some embodiments, the object can include one or more first cells and the reference object can include one or more second cells.

In some embodiments, method 800 can include detecting one or more vibrations of a support device (e.g., support device 204) with one or more sensors (e.g., XYZ accelerometers 206R) coupled to the support device.

In some embodiments, method 800 can include synchronizing the first and second digital representations (e.g., using clocks 120P, 120R as described with respect to FIG. 1).

While placing cells/living tissue in the principal signal path has been discussed herein, it should be understood that any object can be placed in the principal signal path to determine the vibrational spectra and/or other characteristics of the object, with noise removed from output data using CPNR. Accordingly, the CPNR embodiments disclosed herein are not limited to determining vibrational spectra for cells/living tissue and may be applied in any field.

Further, while a principal signal path and single reference signal path have been shown, any number of reference signal paths can be included, such as two, three, four, or five reference signal paths. In some embodiments, multiple detectors and/or filters can be used simultaneously, for example, to determine vibrational spectra for different wavelengths bands. This may assist in simultaneously determining vibrational spectra for various cells and/or various cell subcomponents. In some embodiments, modulation of photon beam intensity in a controlled fashion either through a phase lock loop or by other means can be used to improve the data extracted from the measurements, in particular to improve the signal-to-noise ratio. Accordingly, the CPNR embodiments disclosed herein may be used alongside any known noise reduction techniques.

Finally, while a principal signal path that includes an object (e.g., cells/living tissue) and a reference signal path that includes a reference medium with no cells/living tissue have been discussed, in some embodiments, the reference signal path can also include a reference object (e.g., the reference medium can include cells/living tissue). In such embodiments, data from the reference signal path gathered as described herein may be compared to data from the principal signal path gathered as described herein to identify differences between how a reference object (e.g., normal cells) in the reference signal path modulates a reference photon beam as compared to how an object (e.g., abnormal cells) in the principal signal path modulates a principal photon beam.

For example, the modulated reference photon beam and modulated principal photon beam may be converted to a reference digital representation and a principle digital representation, respectively, using the components and methods discussed herein. Then, the reference and principle digital representations may be analyzed and compared as disclosed herein to remove from the principle digital representation any matching events that correspond (within specified deltas as discussed herein) to reference events in the reference digital representation, or vice versa. The resulting digital representation may be a noise-filtered digital representation of the differences between the vibrational spectra of the cells/living tissue in the principal signal path and the vibrational spectra of the cells/living tissue in the reference signal path with little to no noise. In some embodiments, cells in the principal signal path and cells in the reference signal path may be the same or substantially the same type of cells (e.g., brain cells and/or cells from the same portion of a living organism). In some embodiments, some unique categorization can exist between the cells in the principal signal path and the cells in the reference signal path (e.g., GBM brain cells in the principal signal path can be compared to healthy brain cells in the reference signal path). In such cases, the differences between the vibrational spectra can be indicative of a unique categorization (e.g. GBM brain cells).

In some embodiments, characteristics of events that remain after performing such a cell-to-cell comparison and removal ("categorization events") may be used to identify cells of a particular category (e.g., GBM brain cells) during a subsequent examination of cells. In some embodiments, the categorization events can be events that remain after multiple cell-to-cell comparisons and matching event removals described above. Time, frequency, and/or amplitude characteristics of the categorization events can be recorded. Then, the identification of matching events from a subsequent examination of cells (e.g., events in a noise-filtered digital representation of the vibrational spectra of the cells obtained using CPNR as described herein) that correspond to one or more categorization events based on the time, frequency, and/or amplitude characteristics (e.g., that have time, frequency, and/or amplitude characteristics within predetermined ranges as discussed herein) can indicate that the cells being subsequently examined correspond to a particular category of cells (e.g., GBM brain cells). In some embodiments, the number of matching events and/or the similarities between events from the subsequent examination of the cells and the categorization events (e.g., deltas between time, frequency, and/or amplitude characteristics) may indicate a likelihood that the cells being subsequently examined correspond to the particular category of cells. In some embodiments, the one or more processors described herein (e.g., processor(s) 110) may be configured to calculate a confidence score based on the number of matching events and/or similarities between events from the subsequent examination of the cells and the categorization events, for example, the confidence score indicating a likelihood that the cells being subsequently examined correspond to the particular category of cells.

The disclosed systems and methods obtain the benefit of more accurately studying cells/tissue in vitro, as signal noise can be reduced and vibrational spectra of cells/living tissue and/or subcomponents of a cell can be more precisely measured and characterized. Additionally, the systems can be configured such that even extended observations do not harm cells, as more accurate readings enable lower light intensities to be used.

Example Computing System

Figure 9:
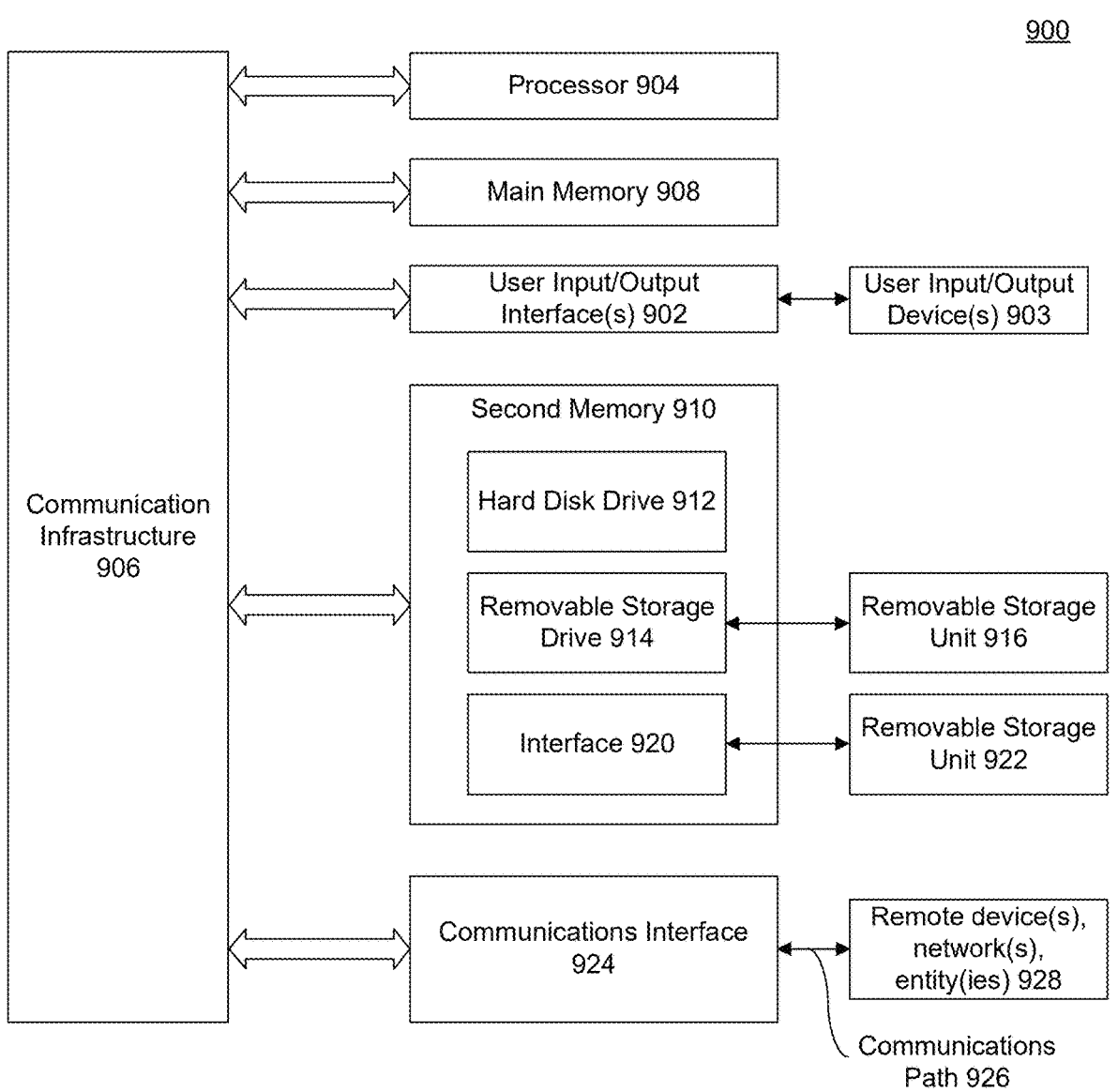
FIG. 9 illustrates an example computer system useful for implementing various embodiments.

FIG. 9 depicts an example computing system useful for implementing various embodiments.

Various embodiments can be implemented, for example, using one or more well-known computing systems, such as computing system 900 shown in FIG. 9. One or more computing systems 900 can be used, for example, to implement any of the embodiments discussed herein, as well as combinations and sub-combinations thereof. For example, the example computing system can be implemented as part of computer and monitor 371 or one or more computers implementing processor(s) 110, 210. Cloud implementations may include one or more of the example computing systems operating locally or distributed across one or more server sites.

Computing system 900 can include one or more processors (also called central processing units, or CPUs), such as a processor 904. Processor 904 can be connected to a communication infrastructure or bus 906.

Computing system 900 can also include customer input/output device(s) 902, such as monitors, keyboards, pointing devices, etc., which can communicate with communication infrastructure 906 through customer input/output interface(s) 902.

One or more of processors 904 can be a graphics processing unit (GPU). In some embodiments, a GPU can be a processor that is a specialized electronic circuit designed to process mathematically intensive applications. The GPU can have a parallel structure that is efficient for parallel processing of large blocks of data, such as mathematically intensive data common to computer graphics applications, images, videos, etc.

Computing system 900 can also include a main or primary memory 908, such as random access memory (RAM). Main memory 908 can include one or more levels of cache. Main memory 908 can have stored therein control logic (i.e., computer software) and/or data.

Computing system 900 can also include one or more secondary storage devices or memory 910. Secondary memory 910 can include, for example, a hard disk drive 912 and/or a removable storage device or drive 914. Removable storage drive 914 can be a floppy disk drive, a magnetic tape drive, a compact disk drive, an optical storage device, tape backup device, and/or any other storage device/drive.

Removable storage drive 914 can interact with a removable storage unit 916. Removable storage unit 916 can include a computer usable or readable storage device having stored thereon computer software (control logic) and/or data. Removable storage unit 916 can be a floppy disk, magnetic tape, compact disk, DVD, optical storage disk, and/any other computer data storage device. Removable storage drive 914 can read from and/or write to removable storage unit 916.

Secondary memory 910 can include other means, devices, components, instrumentalities, or other approaches for allowing computer programs and/or other instructions and/or data to be accessed by computing system 900. Such means, devices, components, instrumentalities or other approaches can include, for example, a removable storage unit 922 and an interface 920. Examples of the removable storage unit 922 and the interface 920 can include a program cartridge and cartridge interface (such as that found in video game devices), a removable memory chip (such as an EPROM or PROM) and associated socket, a memory stick and USB port, a memory card and associated memory card slot, and/or any other removable storage unit and associated interface.

Computing system 900 can further include a communication or network interface 924. Communication interface 924 can enable computing system 900 to communicate and interact with any combination of external devices, external networks, external entities, etc. (individually and collectively referenced by reference number 928). For example, communication interface 924 can allow computing system 900 to communicate with external or remote devices 928 over communications path 926, which can be wired and/or wireless (or a combination thereof), and which can include any combination of LANs, WANs, the Internet, etc. Control logic and/or data can be transmitted to and from computing system 900 via communication path 926.

Computing system 900 can also be any of a personal digital assistant (PDA), desktop workstation, laptop or notebook computer, netbook, tablet, smart phone, smart watch or other wearable, appliance, part of the Internet-of-Things, and/or embedded system, to name a few non-limiting examples, or any combination thereof.

Computing system 900 can be a client or server, accessing or hosting any applications and/or data through any delivery paradigm, including but not limited to remote or distributed cloud computing solutions; local or on-premises software ("on-premise" cloud-based solutions); "as a service" models (e.g., content as a service (CaaS), digital content as a service (DCaaS), software as a service (SaaS), managed software as a service (MSaaS), platform as a service (PaaS), desktop as a service (DaaS), framework as a service (FaaS), backend as a service (BaaS), mobile backend as a service (MBaaS), infrastructure as a service (IaaS), etc.); and/or a hybrid model including any combination of the foregoing examples or other services or delivery paradigms.

Any applicable data structures, file formats, and schemas in computing system 900 can be derived from standards including but not limited to JavaScript Object Notation (JSON), Extensible Markup Language (XML), Yet Another Markup Language (YAML), Extensible Hypertext Markup Language (XHTML), Wireless Markup Language (WML), MessagePack, XML Customer Interface Language (XUL), or any other functionally similar representations alone or in combination. Alternatively, proprietary data structures, formats or schemas may be used, either exclusively or in combination with known or open standards.

In some embodiments, a tangible, non-transitory apparatus or article of manufacture comprising a tangible, non-transitory computer useable or readable medium having control logic (software) stored thereon may also be referred to herein as a computer program product or program storage device. This can include, but is not limited to, computing system 900, main memory 908, secondary memory 910, and removable storage units 916 and 922, as well as tangible articles of manufacture embodying any combination of the foregoing. Such control logic, when executed by one or more data processing devices (such as computing system 900), can cause such data processing devices to operate as described herein.

Based on the teachings contained in this disclosure, it will be apparent to persons skilled in the relevant art(s) how to make and use embodiments of this disclosure using data processing devices, computing systems and/or computing architectures other than those shown in FIGS. 1, 2, and 9. In particular, embodiments can operate with software, hardware, and/or operating system implementations other than those described herein.

CONCLUSION

It is to be understood that while certain embodiments of the disclosure have been illustrated and described herein, the claims are not to be limited to the specific forms or arrangement of parts described and shown. Modifications and variations of the disclosure are possible considering the above teachings. It is therefore to be understood that the disclosure may be practiced otherwise than as specifically described.

What is claimed is:

1. A system for measuring vibrational spectra of objects, the system comprising:

at least one photon source configured to generate a first photon beam and a second photon beam;

a support device configured to support the objects in a medium and a reference medium such that, in operation, the first photon beam passes through the objects, thereby directly modulating the first photon beam, and the second photon beam passes through the reference medium modulating the second photon beam;

at least one detector configured to detect the modulated first and second photon beams and produce first and second analog signals representative of the resultant vibrational spectra of the objects in the medium and the resultant noise spectra of the reference medium;

at least one analog-to-digital converter configured to convert the first and second analog signals into first and second digital representations; and at least one processor configured to perform operations comprising:

defining one or more reference events from the second digital representation, each of the one or more reference events comprising a time characteristic, a frequency characteristic, or an amplitude characteristic;

identifying one or more matching events from the first digital representation, each of the one or more matching events corresponding to a reference event of the one or more reference events; and removing the one or more matching events from the first digital representation, thereby outputting a noise-filtered digital representation of the vibrational spectra of the objects.

2. The system of claim 1, further comprising one or more sensors coupled to the support device and configured to detect one or more vibrations of the support device.

3. The system of claim 1, wherein the at least one photon source comprises a light-emitting diode (LED), a laser, or a combination thereof.

4. The system of claim 1, wherein the at least one detector comprises a single pixel or multiple pixel detector configured to operate over a broad frequency range.

5. The system of claim 1, wherein the at least one detector comprises a photon detector.

6. The system of claim 1, wherein the at least one photon source, the at least one detector, the at least one analog-to-digital converter, or a combination thereof receives power from a DC battery power source or a low-noise DC power supply for noise reduction.

7. The system of claim 1, wherein the operations further comprise defining the one or more reference events with a precision measuring matrix (PMM).

8. The system of claim 1, wherein the support device comprises a heater configured to regulate a temperature of the objects and the reference medium.

9. The system of claim 1, wherein the support device comprises one or more wetted special slips (WSS) disposed on the objects in the medium and/or the reference medium so as to eliminate surface tension modulation of the first and second photon beams.

10. The system of claim 1, wherein the at least one processor is further configured to define one or more reference events from the second digital representation that have harmonic characteristics.

11. The system of claim 1, wherein the objects comprise at least one sub-cellular structure of living tissue having a fluorescent marker, such that the living tissue modulates the first photon beam thereby causing the at least one sub-cellular structure to emit photons at a wavelength longer than a wavelength of the first photon beam, and the system further comprises a filter to pass only the emitted photons associated with the at least one sub-cellular structure.

12. The system of claim 1, wherein:

the reference medium comprises a reference object such that the noise spectra comprises a vibrational spectra of the reference object, and the noise-filtered digital representation comprises a noise-filtered digital representation of differences between the vibrational spectra of the objects and the vibrational spectra of the reference object.

13. The system of claim 12, wherein the objects comprise one or more first cells and the reference object comprises one or more second cells.

14. A method for measuring vibrational spectra of an objects, the method comprising:

generating a first photon beam and a second photon beam;

passing the first photon beam through the objects in a medium and the second photon beam through a reference medium, thereby directly modulating the first and second photon beams;

detecting the modulated first and second photon beams and producing first and second analog signals representative of the resultant vibrational spectra of the objects in the medium and the resultant noise spectra of the reference medium, respectively;

converting the first and second analog signals into first and second digital representations, respectively;

defining one or more reference events from the second digital representation, each of the one or more reference events comprising a time characteristic, a frequency characteristic, or an amplitude characteristic;

identifying one or more matching events from the first digital representation, each of the one or more matching events corresponding to a reference event of the one or more reference events; and removing the one or more matching events from the first digital representation, thereby outputting a noise-filtered digital representation of the vibrational spectra of the objects.

15. The method of claim 14, further comprising detecting one or more vibrations of a support device with one or more sensors coupled to the support device.

16. The method of claim 14, wherein defining the one or more reference events comprises:

mapping the second digital representation to one or more partials, each partial representing an amplitude specified over a specific frequency range and time period; and chaining the one or more partials into the one or more reference events, wherein the mapping and chaining are performed using a precision measuring matrix (PMM).

17. The method of claim 14, wherein:

the time characteristic of a reference event comprises a start time of the reference event, an end time of the reference event, a duration of the reference event, an absolute start time of the reference event, or a combination thereof, and identifying the one or more matching events comprises identifying a matching event comprising a matching time characteristic, the matching time characteristic comprising a start time within a predetermined range from the start time of the reference event, an end time within a predetermined range from the end time of the reference event, a duration within a predetermined range from the duration of the reference event, an absolute start time within a predetermined range from the absolute start time of the reference event, or a combination thereof.

18. The method of claim 17, further comprising categorizing the reference event as a transient reference event, wherein the matching time characteristic comprises the absolute start time within a predetermined range from the absolute start time of the reference event.

19. The method of claim 17, further comprising categorizing the reference event as a static reference event, wherein the matching time characteristic comprises the duration within a predetermined range from the duration of the reference event.

20. The method of claim 14, wherein:

the frequency characteristic of a reference event comprises a start frequency of the reference event, an end frequency of the reference event, a lower frequency of the reference event, an upper frequency of the reference event, a delta between the lower and upper frequencies of the reference event, or a combination thereof; and identifying the one or more matching events comprises identifying a matching event comprising a matching frequency characteristic, the matching frequency characteristic comprising a start frequency within a predetermined range from the start frequency of the reference event, an end frequency within a predetermined range from the end frequency of the reference event, a lower frequency within a predetermined range from the lower frequency of the reference event, an upper frequency within a predetermined range from the upper frequency of the reference event, a delta between the lower and upper frequencies within a predetermined range from the delta between the lower and upper frequencies of the reference event, or a combination thereof.

21. The method of claim 14, wherein:

the amplitude characteristic of a reference event comprises a start amplitude of the reference event, an end amplitude of the reference event, a lower amplitude of the reference event, an upper amplitude of the reference event, a delta between the lower and upper amplitudes of the reference event, or a combination thereof; and identifying the one or more matching events comprises identifying a matching event comprising a matching amplitude characteristic, the matching amplitude characteristic comprising a start amplitude within a predetermined range from the start amplitude of the reference event, an end amplitude within a predetermined range from the end amplitude of the reference event, a lower amplitude within a predetermined range from the lower amplitude of the reference event, an upper amplitude within a predetermined range from the upper amplitude of the reference event, a delta between the lower and upper amplitudes within a predetermined range from the delta between the lower and upper amplitudes of the reference event, or a combination thereof.

22. The method of claim 14, wherein defining the one or more reference events comprises categorizing the one or more reference events into at least one domain, the at least one domain comprising a time domain, a frequency domain, an amplitude domain, a harmonic domain, a partial chain domain, a memory domain, a non-random domain, or a combination thereof.

23. The method of claim 22, wherein identifying the one or more matching events comprises comparing a categorized reference event to an event from the first digital representation that shares at least one domain with the categorized reference event, prior to identifying the event as a matching event.

24. The method of claim 14, further comprising synchronizing the first and second digital representations.

25. The method of claim 14, wherein reference events each corresponding to a frequency delta, an amplitude delta, and a time delta are detected in the second digital representation such that the detected reference events are used to search through the first digital representation, and, if matching events each having a frequency within a frequency delta corresponding to a reference event, an amplitude within an amplitude delta corresponding to the reference event, and a time within a time delta corresponding to the reference event are detected, the matching events are removed from the first digital representation.

26. The method of claim 14, further comprising comparing a vibrational spectra of a reference object of the reference medium to the vibrational spectra of the objects such that the noise-filtered digital representation comprises a noise-filtered digital representation of differences between the vibrational spectra of the objects and the vibrational spectra of the reference object.

27. The method of claim 26, wherein the objects comprise one or more first cells and the reference object comprises one or more second cells.

28. The method of claim 14, wherein the passing of the first and second beams further comprises passing the first or second beams through a wetted special slips (WSS) prior to passing through the objects in the medium or the reference medium, respectively, to eliminate surface tension modulation of the first and second photon beams.

29. The method of claim 14, further defining one or more reference events from the second digital representation that have harmonic characteristics.

* * * * *